(12) United States Patent
Church et al.

(10) Patent No.: US 6,485,944 B1
(45) Date of Patent: Nov. 26, 2002

(54) REPLICA AMPLIFICATION OF NUCLEIC ACID ARRAYS

(75) Inventors: George M. Church, Brookline, MA (US); Rob Mitra, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/267,496

(22) Filed: Mar. 12, 1999

Related U.S. Application Data

(63) Continuation-in-part of application No. 09/143,014, filed on Aug. 28, 1998.
(60) Provisional application No. 60/061,511, filed on Oct. 10, 1997, and provisional application No. 60/076,570, filed on Mar. 2, 1998.

(51) Int. Cl.$^7$ .......................... C12P 19/34; C12Q 1/68; G01N 1/00; G01N 15/00
(52) U.S. Cl. ........................ 435/91.2; 435/6; 435/91.1; 422/50; 422/68.1
(58) Field of Search ........................ 435/6, 91.1, 91.2; 422/50, 68.1

(56) References Cited

U.S. PATENT DOCUMENTS

| | | | |
|---|---|---|---|
| 4,591,567 A | 5/1986 | Britten et al. ................ | 435/293 |
| 4,731,325 A | 3/1988 | Palva et al. ..................... | 435/6 |
| 4,863,849 A | 9/1989 | Melamede ...................... | 435/6 |
| 4,981,783 A | 1/1991 | Augenlicht .................... | 435/6 |
| 5,188,963 A | 2/1993 | Stapleton .................... | 435/299 |
| 5,302,509 A | 4/1994 | Cheeseman .................... | 435/6 |
| 5,306,619 A | 4/1994 | Edwards et al. ................ | 435/6 |
| 5,324,633 A | 6/1994 | Fodor et al. .................... | 435/6 |
| 5,328,825 A | 7/1994 | Warren, III et al. ............ | 435/6 |
| 5,382,511 A | 1/1995 | Stapleton .................... | 435/6 |
| 5,405,746 A | 4/1995 | Uhlen .......................... | 435/6 |
| 5,424,186 A | 6/1995 | Fodor et al. .................... | 435/6 |
| 5,426,180 A | 6/1995 | Kool .......................... | 536/25.3 |
| 5,437,976 A | 8/1995 | Utermohlen .................... | 435/6 |
| 5,445,934 A | 8/1995 | Fodor et al. .................... | 435/6 |
| 5,451,500 A | 9/1995 | Stapleton .................... | 435/6 |
| 5,484,702 A | 1/1996 | Ludwig .......................... | 435/6 |
| 5,506,350 A | 4/1996 | Bittner et al. ............... | 536/55.3 |
| 5,510,270 A | 4/1996 | Fodor et al. ................ | 436/518 |
| 5,527,681 A | 6/1996 | Holmes .......................... | 435/6 |
| 5,545,531 A | 8/1996 | Rava et al. .................... | 435/6 |
| 5,552,270 A | 9/1996 | Khrapko et al. ................ | 435/6 |
| 5,556,752 A | 9/1996 | Lockhart et al. ................ | 435/6 |
| 5,571,639 A | 11/1996 | Hubbell et al. ................ | 430/5 |
| 5,578,444 A | 11/1996 | Edwards et al. ................ | 435/6 |
| 5,578,832 A | 11/1996 | Trulson et al. ............ | 250/458.1 |
| 5,587,128 A | 12/1996 | Wilding et al. ................ | 422/50 |
| 5,593,839 A | 1/1997 | Hubbell et al. ................ | 435/6 |
| 5,599,695 A | 2/1997 | Pease et al. ............... | 435/91.1 |
| 5,616,478 A | 4/1997 | Chetverin et al. .......... | 435/91.2 |
| 5,631,134 A | 5/1997 | Cantor .......................... | 435/6 |
| 5,641,658 A | 6/1997 | Adams et al. .............. | 435/91.2 |
| 5,653,939 A | 8/1997 | Hollis et al. .................... | 422/50 |
| 5,795,714 A | 8/1998 | Cantor et al. .................... | 435/6 |
| 6,017,738 A * | 1/2000 | Morris et al. .............. | 435/91.2 |
| 6,274,351 B1 * | 8/2001 | Peponnet .................... | 435/91.1 |

FOREIGN PATENT DOCUMENTS

| | | |
|---|---|---|
| EP | 0 895 082 A2 | 2/1999 |
| WO | WO 93/17126 | 9/1993 |
| WO | WO 96/28457 | 9/1996 |
| WO | WO 96/36731 | 11/1996 |
| WO | WO 97/09449 | 3/1997 |
| WO | WO 97/10365 | 3/1997 |
| WO | WO 98/29736 | 7/1998 |
| WO | WO 98/44151 | 10/1998 |
| WO | WO 98/44152 | 10/1998 |

OTHER PUBLICATIONS

Malpiece et al., 1984, Experientia, 40: 483–485.
Duggan et al., "Expression profiling using cDNA microarrays," *Nature Genetics Supplement*, 21:10–14 (1999).
Schena et al., "Quantitative Monitoring of Gene Expression Patterns with a Complementary DNA Microarray," *Science*, 270:467–470 (1995).

* cited by examiner

*Primary Examiner*—Ardin H. Marschel
(74) *Attorney, Agent, or Firm*—Banner & Witcoff, Ltd.

(57) ABSTRACT

Disclosed are improved methods of making and using immobilized arrays of nucleic acids, particularly methods for producing replicas of such arrays. Included are methods for producing high density arrays of nucleic acids and replicas of such arrays, as well as methods for preserving the resolution of arrays through rounds of replication. Also included are methods which take advantage of the availability of replicas of arrays for increased sensitivity in detection of sequences on arrays. Improved methods of sequencing nucleic acids immobilized on arrays utilizing single copies of arrays and methods taking further advantage of the availability of replicas of arrays are disclosed. The improvements lead to higher fidelity and longer read lengths of sequences immobilized on arrays. Methods are also disclosed which improve the efficiency of multiplex PCR using arrays of immobilized nucleic acids.

28 Claims, No Drawings

REPLICA AMPLIFICATION OF NUCLEIC ACID ARRAYS

This application is a continuation-in-part of U.S. patent application Ser. No. 09/143,014, filed Aug. 28, 1998; which claims the benefit of the filing date of U.S. Provisional Application No. 60/061,511, filed Oct. 10, 1997; and U.S. Provisional Application No. 60/076,570, filed Mar. 2, 1998.

FIELD OF THE INVENTION

The invention relates in general to the reproducible, mass-production of nucleic acid arrays. The invention also relates to methods of sequencing nucleic acids on arrays.

BACKGROUND OF THE INVENTION

Arrays of nucleic acid molecules are of enormous utility in facilitating methods aimed at genomic characterization (such as polymorphism analysis and high-throughput sequencing techniques), screening of clinical patients or entire pedigrees for the risk of genetic disease, elucidation of protein/DNA- or protein/protein interactions or the assay of candidate pharmaceutical compounds for efficacy; however, such arrays are both labor-intensive and costly to produce by conventional methods. Highly ordered arrays of nucleic acid fragments are known in the art (Fodor et al., U.S. Pat. No. 5,510,270; Lockhart et al., U.S. Pat. No. 5,556,752).

Chetverin and Kramer (WO 93/17126) are said to disclose a highly ordered array which may be amplified.

U.S. Pat. No. 5,616,478 of Chetverin and Chetverina reportedly claims methods of nucleic acid amplification, in which pools of nucleic acid molecules are positioned on a support matrix to which they are not covalently linked. Utermohlen (U.S. Pat. No. 5,437,976) is said to disclose nucleic acid molecules randomly immobilized on a reusable matrix.

There is need in the art for improved methods of nucleic acid array design and production. There is also a need in the art for methods with improved resolution and/or sensitivity for detection of sequences on nucleic acid arrays. There is also a need in the art for improved methods of sequencing the molecules on nucleic acid arrays.

SUMMARY OF THE INVENTION

The invention provides a method of producing a high density array of immobilized nucleic acid molecules, such method comprising the steps of: 1) creating an array of spots of a nucleic acid capture activity such that the spots of said capture activity are separated by a distance greater than the diameter of the spots, and the size of the spots is less than the diameter of the excluded volume of the nucleic acid molecule to be captured; 2) contacting the array of spots of nucleic acid capture activity with an excess of nucleic acid molecules with an excluded volume diameter greater than the diameter of the spots of nucleic acid capture activity, resulting in an immobilized array of nucleic acid molecules in which each spot of nucleic acid capture activity can bind only one nucleic acid molecule with an excluded volume diameter greater than the size of said spots of nucleic acid capture activity.

In a preferred embodiment of the invention, the nucleic acid capture activity may be a hydrophobic compound, an oligonucleotide, an antibody or fragment of an antibody, a protein, a peptide, an intercalator, biotin, avidin, or streptavidin.

In another embodiment of the invention the immobilized array of spots of a nucleic acid capture activity are arranged in a predetermined geometry.

In another embodiment, the immobilized spots of a nucleic acid capture activity are aligned with other microfabricated features.

The invention also encompasses a method of making a plurality of a high-density nucleic acid array made using spots of nucleic acid capture activity as described above.

The invention provides a method for the detection of a nucleic acid on an array of nucleic acid molecules, such method comprising the steps of generating a plurality of a nucleic acid molecule array wherein the nucleic acid molecules of each member of said plurality occupy positions which correspond to those positions occupied by the nucleic acid molecules of each other member of said plurality of a nucleic acid array, and subjecting one or more members of said plurality, but at least one less than the total number of said plurality to a method of signal detection comprising a signal amplification method which renders said member of said plurality of a nucleic acid array non-reusable.

It is preferred that the signal amplification method comprises fluorescence measurement.

In a preferred embodiment the method of detection of a nucleic acid on an array of nucleic acid molecules detects the amount of an RNA expressed in a first RNA-containing nucleic acid population relative to that expressed in a second RNA-containing nucleic acid population. The method further comprises the steps of preparing a first population of fluorescently labeled cDNA using said first population of RNA containing nucleic acid as a template, preparing a second fluorescently labeled cDNA population using said second population of RNA-containing nucleic acid as a template, said second fluorescently labeled cDNA population being labeled with a fluorescent label distinguishable from that used to label said first population, contacting a mixture of said first fluorescently labeled cDNA population and said second fluorescently labeled cDNA population with a member of said plurality of nucleic acid arrays under conditions which permit hybridization of said fluorescently labeled cDNA populations with nucleic acids immobilized on said members of said plurality of nucleic acid arrays and detecting the fluorescence of said first fluorescently labeled population of cDNA and the fluorescence of said second fluorescently labeled population of cDNA hybridized to said member of said plurality of nucleic acid arrays, wherein the relative amount of said first fluorescent label and said second fluorescent label detected on a given nucleic acid feature of said array indicates the relative level of expression of RNA derived from the nucleic acid of that feature in the mRNA-containing cDNA populations tested.

In another embodiment the method of detection of a nucleic acid on an array of nucleic acid molecules detects the amount of an RNA expressed in a first RNA-containing nucleic acid population relative to that expressed in a second RNA-containing nucleic acid population. The method further comprises the steps of preparing a first population of fluorescently labeled cDNA using said first population of RNA containing nucleic acid as a template, preparing a second fluorescently labeled cDNA population using said second population of RNA-containing nucleic acid as a template, contacting said first fluorescently labeled cDNA population with one member of a plurality of immobilized nucleic acid arrays under conditions which permit hybridization of said fluorescently labeled cDNA population with nucleic acid immobilized on said member of a plurality of immobilized nucleic acid arrays, contacting said second flourescently labeled cDNA population with another member of the same plurality of immobilized nucleic acid arrays under conditions which permit hybridization of said fluorescently labeled cDNA populations with nucleic acid immobilized on said members of a plurality of immobilized nucleic acid arrays, detecting the intensity of fluorescence on each member of said plurality contacted with a fluorescently labeled cDNA population, and comparing the intensity of fluorescence detected on each member of said plurality of immobilized nucleic acid arrays so tested, to determine the relative expression of mRNA derived from those nucleic acids on the array in the mRNA-containing cDNA populations tested.

The invention provides a method of preserving the resolution of nucleic acid features on a first immobilized array during cycles of array replication, said method comprising the steps of: a) amplifying the features of a first array to yield an array of features with a hemispheric radius, r, and a cross-sectional area, q, at the surface supporting said array, such that said features remain essentially distinct; b) contacting said array of features with a radius, r, with a support, maintained at a fixed distance from said first array, said fixed distance less than r, and such that the cross-sectional area of the hemispheric feature, measured at said fixed distance from the surface supporting said first array is less than q, and such that at least a subset of nucleic acid molecules produced by said amplifying are transferred to said support; c) covalently affixing said nucleic acid molecules to said support to form a replica of said first immobilized array, wherein the positions of said nucleic acid molecules on said replica correspond to the positions of said nucleic acid molecules of said first array from which they were amplified, and wherein the areas occupied on the surface of said support by the individual features of said replica are less than the areas occupied on the surface supporting said first immobilized array.

It is preferred that said amplifying be performed by PCR.

In another embodiment of the method of preserving the resolution of nucleic acid features on a first immobilized array during cycles of array replication, the method is repeated to yield further replicas with preserved resolution.

The invention provides a method for determining the nucleotide sequence of the features of an immobilized nucleic acid array, such method comprising the steps of: a) ligating a first double-stranded nucleic acid probe to one end of a nucleic acid of a feature of said array, said first double stranded nucleic acid probe having a restriction endonuclease recognition site for a restriction endonuclease whose cleavage site is separate from its recognition site and which generates a protruding strand upon cleavage; b) identifying one or more nucleotides at the end of said polynucleotide by the identity of the first double stranded nucleic acid probe ligated thereto or by extending a strand of the polynucleotide or probe; c) amplifying the features of said array using a primer complementary to said first double stranded nucleic acid probe, such that only molecules which have been successfully ligated with said first double stranded nucleic acid probe are amplified to yield an amplified array; d) contacting said amplified array with support such that at least a subset of nucleic acid molecules produced by said amplifying are transferred to said support; e) covalently attaching said subset of nucleic acid molecules to said support to form a replica of said amplified array; f) cleaving the nucleic acid features of the array with a nuclease recognizing said nuclease recognition site of said probe such that the nucleic acid of the features is shortened by one or more nucleotides; and g) repeating steps (a)–(f) until the nucleotide sequences of the features of said array are determined.

It is preferred that the nucleic acid probe comprises four components, each component being capable of indicating the presence of a different nucleotide in the protruding strand upon ligation. It is further preferred that each of the components of the probe is labeled with a different fluorescent dye and that the different fluorescent dyes are spectrally resolvable.

In another embodiment of the invention, the features of the array are amplified after step (e) and before step (f).

It is preferred that the amplifying be accomplished by PCR.

In another embodiment, the method of determining the sequence of the features of an immobilized nucleic acid array is modified such that: i) after one or more cycles using said first double stranded nucleic acid probe in step (a), a distinct nucleic acid probe is used, in place of said first double stranded nucleic probe, said distinct nucleic acid probe comprising a restriction endonuclease recognition site for a restriction endonuclease whose cleavage site is separated from its recognition site, said distinct nucleic acid probe also comprising sequences such that a primer complementary to said distinct nucleic acid probe will not hybridize with said first double stranded nucleic acid probe; and ii) a primer complementary to said distinct nucleic acid probe is used in place of said primer complementary to said first double stranded nucleic acid probe in step (c), so that selective amplification of those features which successfully completed the previous cycle of restriction and ligation occurs.

In another embodiment of this modified method of determining the nucleotide sequence of the features of an immobilized nucleic acid array, a new distinct nucleic acid probe is used after each cycle of restriction and ligation, said new distinct nucleic acid probe comprising a sequence such that a primer complementary to that sequence will not hybridize to any probe used in previous cycles.

The invention provides a method of determining the nucleotide sequence of the features of an array of immobilized nucleic acids comprising the steps of: a) adding a mixture comprising an oligonucleotide primer and a template-dependent polymerase to an array of immobilized nucleic acid features under conditions permitting hybridization of the primer to the immobilized nucleic acids; b) adding a single, fluorescently labeled deoxynucleoside triphosphate to the mixture under conditions which permit incorporation of the labeled deoxynucleotide onto the 3' end of the primer if it is complementary to the next adjacent base in the sequence to be determined; c) detecting incorporated label by monitoring fluorescence; d) repeating steps (b)–(c) with each of the remaining three labeled deoxynucleoside triphosphates in turn; and e) repeating steps (b)–(d) until the nucleotide sequence is determined.

In a preferred embodiment, the primer, buffer and polymerase are cast into a polyacrylamide gel bearing the array of immobilized nucleic acids.

It is preferred that the single fluorescently labeled deoxynucleotide further comprises a mixture of the single deoxynucleoside triphosphate in labeled and unlabeled forms.

In another embodiment, the additional step of photobleaching said array is performed after step (d) and before step (e).

In another embodiment, the fluorescently labeled deoxynucleoside triphosphates are labeled with a cleavable linkage to the fluorophore, and the additional step of cleaving said linkage to the fluorophore is performed after step (d) and before step (e). In another embodiment, the oligonucleotide primer comprises sequences permitting formation of a hairpin loop.

In another embodiment, after a predetermined number of cycles of steps (b)–(d), a defined regimen of deoxynucleotide and chain-terminating deoxynucleotide analog addition is performed, such that out-of-phase molecules are blocked from further extension cycles, said regimen followed by continued cycles of steps (b)–(d) until the nucleotide sequence of the features of the array is determined.

The invention provides a method of determining the nucleotide sequence of the features of an array of immobilized nucleic acids comprising the steps of: a) adding a mixture comprising an oligonucleotide primer and a template-dependent polymerase to an array of immobilized nucleic acid features under conditions permitting hybridization of the primer to the immobilized nucleic acids; b) adding a first mixture of three unlabeled deoxynucleoside triphosphates under conditions which permit incorporation of deoxynucleotides to the end of the primer if they are complementary to the next adjacent base in the sequence to be determined; c) adding a second mixture of three unlabeled deoxynucleoside triphosphates, along with buffer and polymerase if necessary, said second mixture comprising the deoxynucleoside triphosphate not included in the mixture of step (b), under conditions which permit incorporation of deoxynucleotides to the end of the primer if they are complementary to the next adjacent base in the sequence to be determined; d) repeating steps (b)–(c) for a predetermined number of cycles; e) adding a single, fluorescently labeled deoxynucleoside triphosphate to the mixture under conditions which permit incorporation of the labeled deoxynucleotide onto the 3' terminus of the primer if it is complementary to the next adjacent base in the sequence to be determined; f) detecting incorporated label by monitoring fluorescence; g) repeating steps (e)–(f), with each of the remaining three labeled deoxynucleoside triphosphates in turn; and h) repeating steps (e)–(g) until the nucleotide sequence is determined.

It is preferred that for the first or second mixtures of three unlabeled deoxynucleoside triphosphates, a mixture which comprises deoxyguanosine triphosphate further comprises deoxyadenosine triphosphate.

In a preferred embodiment, method the primer and polymerase are cast into a polyacrylamide gel bearing the array of immobilized nucleic acids.

In a preferred embodiment, the single fluorescently labeled deoxynucleotide further comprises a mixture of the single deoxynucleoside triphosphate in labeled and unlabeled forms.

In another embodiment of this method of determining the nucleotide sequence of nucleic acid features on an array, the additional step of photobleaching the array is performed after step (g) and before step (h).

In another embodiment of this method of determining the nucleotide sequence of nucleic acid features on an array, the fluorescently labeled deoxynucleoside triphosphates are labeled with a cleavable linkage to the fluorophore and after step (g) and before step (h) the additional step of cleaving the linkage to the fluorophore is performed.

In another embodiment of this method of determining the nucleotide sequence of nucleic acid features on an array, the oligonucleotide primer comprises sequences permitting formation of a hairpin loop.

In another embodiment of this method of determining the nucleotide sequence of nucleic acid features on an array, after a predetermined number of cycles of steps (e)–(g), a defined regimen of deoxynucleotide and chain-terminating deoxynucleotide analog addition is performed, such that out-of-phase molecules are blocked from further extension cycles, said regimen followed by continued cycles of steps (e)–(g) until said nucleotide sequence is determined.

The invention provides a method of determining the nucleotide sequence of the features of a micro-array of nucleic acid molecules, said method comprising the steps of: a) creating a micro-array of nucleic acid features in a linear arrangement within and along one side of a polyacrylamide gel, said gel further comprising one or more oligonucleotide primers, and a template-dependent polymerizing activity; b) amplifying the microarray; c) adding a mixture of deoxynucleoside triphosphates, said mixture comprising each of the four deoxynucleoside triphosphates dATP, dGTP, dCTP and dTTP, said mixture further comprising chain-terminating analogs of each of the deoxynucleoside triphosphates dATP, dGTP, dCTP and dTTP, and said chain-terminating analogs each distinguishably labeled with a spectrally distinguishable fluorescent moiety; d) incubating said mixture with said micro-array under conditions permitting extension of said one or more oligonucleotide primers; e) electrophoretically separating the products of said extension within said polyacrylamide gel; and f) determining the nucleotide sequence of the features of said micro-array by detecting the fluorescence of the extended, terminated and separated reaction products within the gel.

It is preferred that the amplifying be performed by PCR.

In another embodiment, the amplifying may be performed by an isothermal method.

In another embodiment the microarray of nucleic acid features in a linear arrangement is derived as a replica of features arranged on a chromosome.

In another embodiment the microarray of nucleic acid features in a linear arrangement is derived as a replica of one linear subset of features on a separate, non-linear microarray of nucleic acid features.

The invention provides a method of simultaneously amplifying a plurality of nucleic acids, said method comprising the steps of: a) creating a micro-array of immobilized oligonucleotide primers; b) incubating the microarray with amplification template and a non-immobilized oligonucleotide primer under conditions allowing hybridization of said template with said oligonucleotide primers; c) incubating the hybridized primers and template with a DNA polymerase activity, and deoxynucleotide triphosphates under conditions permitting extension of the primers; d) repeating steps (b) and (c) for a defined number of cycles to yield a plurality of amplified DNA molecules.

It is preferred that the non-immobilized oligonucleotide primer comprises a pool of oligonucleotide primers comprised of 5' and 3' sequence elements, said 5' sequence element identical in all members of said pool, and said 3' sequence element containing random sequences.

It is preferred that the 5' sequence element comprises a restriction endonuclease recognition sequence.

In another embodiment, the 5' sequence element comprises a transcriptional promoter sequence.

In another embodiment, the immobilized primers are amplified before step (b).

In another embodiment, the immobilized oligonucleotide primers are generated from genomic DNA.

In a preferred embodiment, the microarray, template, non-immobilized primer, and polymerase are cast in a polyacrylamide gel.

As used herein in reference to nucleic acid arrays, the term "plurality" is defined as designating two or more such arrays, wherein a first (or "template") array plus a second array made from it comprise a plurality. When such a plurality comprises more than two arrays, arrays beyond the second array may be produced using either the first array or any copy of it as a template.

As used herein, the terms "randomly-patterned" or "random" refer to a non-ordered, non-Cartesian distribution (in other words, not arranged at pre-determined points along the x- and y axes of a grid or at defined 'clock positions', degrees or radii from the center of a radial pattern) of nucleic acid molecules over a support, that is not achieved through an intentional design (or program by which such a design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon.

As used herein, the terms "immobilized" or "affixed" refer to covalent linkage between a nucleic acid molecule and a support matrix.

As used herein, the term "array" refers to a heterogeneous pool of nucleic acid molecules that is distributed over a support matrix; preferably, these molecules differing in sequence are spaced at a distance from one another sufficient to permit the identification of discrete features of the array.

As used herein, the term "heterogeneous" is defined to refer to a population or collection of nucleic acid molecules that comprises a plurality of different sequences; it is contemplated that a heterogeneous pool of nucleic acid molecules results from a preparation of RNA or DNA from a cell which may be unfractionated or partially-fractionated.

An "unfractionated" nucleic acid preparation is defined as that which has not undergone the selective removal of any sequences present in the complement of RNA or DNA, as the case may be, of the biological sample from which it was prepared. A nucleic acid preparation in which the average molecular weight has been lowered by cleaving the component nucleic acid molecules, but which still retains all sequences, is still "unfractionated" according to this definition, as it retains the diversity of sequences present in the biological sample from which it was prepared.

A "partially-fractionated" nucleic acid preparation may have undergone qualitative size-selection. In this case, uncleaved sequences, such as whole chromosomes or RNA molecules, are selectively retained or removed based upon size. In addition, a "partially-fractionated" preparation may comprise molecules that have undergone selection through hybridization to a sequence of interest; alternatively, a "partially-fractionated" preparation may have had undesirable sequences removed through hybridization. It is contemplated that a "partially-fractionated" pool of nucleic acid molecules will not comprise a single sequence that has been enriched after extraction from the biological sample to the point at which it is pure, or substantially pure.

In this context, "substantially pure" refers to a single nucleic acid sequence that is represented by a majority of nucleic acid molecules of the pool. Again, this refers to enrichment of a sequence in vitro; obviously, if a given sequence is heavily represented in the biological sample, a preparation containing it is not excluded from use according to the invention.

As used herein, the term "biological sample" refers to a whole organism or a subset of its tissues, cells or component parts (e.g. fluids). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as nucleic acid molecules.

As used herein, the term "organism" refers to all cellular life-forms, such as prokaryotes and eukaryotes, as well as non-cellular, nucleic acid-containing entities, such as bacteriophage and viruses.

As used herein, the term "feature" refers to each nucleic acid sequence occupying a discrete physical location on the array; if a given sequence is represented at more than one such site, each site is classified as a feature. In this context, the term "nucleic acid sequence" may refer either to a single nucleic acid molecule, whether double or single-stranded, to a "clone" of amplified copies of a nucleic acid molecule present at the same physical location on the array or to a replica, on a separate support, of such a clone.

As used herein, the term "amplifying" refers to production of copies of a nucleic acid molecule of the array via repeated rounds of primed enzymatic synthesis; "in situ amplification" indicates that such amplifying takes place with the template nucleic acid molecule positioned on a support according to the invention, rather than in solution.

As used herein, the term "support" refers to a matrix upon which nucleic acid molecules of a nucleic acid array are immobilized; preferably, a support is semi-solid.

As used herein, the term "semi-solid" refers to a compressible matrix with both a solid and a liquid component, wherein the liquid occupies pores, spaces or other interstices between the solid matrix elements.

As used herein in reference to the physical placement of nucleic acid molecules or features and/or their orientation relative to one another on an array of the invention, the terms "correspond" or "corresponding" refer to a molecule occupying a position on a second array that is either identical to- or a mirror image of the position of a molecule from which it was amplified on a first array which served as a template for the production of the second array, or vice versa, such that the arrangement of features of the array relative to one another is conserved between arrays of a plurality.

As implied by the above statement, a first and second array of a plurality of nucleic acid arrays according to the invention may be of either like or opposite chirality, that is, the patterning of the nucleic acid arrays may be either identical or mirror-imaged.

As used herein, the term "replica" refers to any nucleic acid array that is produced by a printing process according to the invention using as a template a first randomly-patterned immobilized nucleic acid array.

As used herein, the term "spot" as applied to a component of a microarray refers to a discrete area of a surface containing a substance deposited by mechanical or other means.

As used herein, "excluded volume" refers to the volume of space occupied by a particular molecule to the exclusion of other such molecules.

As used herein, "excess of nucleic acid molecules" refers to an amount of nucleic acid molecules greater than the amount of entities to which such nucleic acid molecules may bind. An excess may comprise as few as one molecule more than the number of binding entities, to twice the number of binding entities, up to 10 times, 100 times, 1000 times the number of binding entities or more.

As used herein, "signal amplification method" refers to any method by which the detection of a nucleic acid is accomplished.

As used herein, a "nucleic acid capture ligand" or "nucleic acid capture activity" refers to any substance which binds nucleic acid molecules, either specifically or non-specifically, or which binds an affinity tag attached to a nucleic acid molecule in such a way as to immobilize the nucleic acid molecule to a support bearing the capture ligand.

As used herein, "replica-destructive" refers to methods of signal amplification which render an array or replica of an array non-reusable.

As used herein, the term "non-reusable," in reference to an array or replica of an array, indicates that, due to the nature of detection methods employed, the array cannot be replicated nor used for subsequent detection methods after the first detection method is performed.

As used herein, the term "essentially distinct" as applied to features of an array refers to the situation where 90% or more of the features of an array are not in contact with other features on the same array.

As used herein, the term "preserved" as applied to the resolution of nucleic acid features on an array means that the features remain essentially distinct after a given process has been performed.

As used herein, the term "distinguishable" as applied to a label, refers to a labeling moiety which can be detected when among other labeling moieties.

As used herein, the term "spectrally distinguishable" or "spectrally resolvable" as applied to a label, refers to a labeling moiety which can be detected by its characteristic fluorescent excitation or emission spectra, one or both of such spectra distinguishing said moiety from other moieties used separately or simultaneously in the particular method.

As used herein, the term "chain-terminating analog" refers to any nucleotide analog which, once incorporated onto the 3' end of a nucleic acid molecule, cannot serve as a substrate for further addition of nucleotides to that nucleic acid molecule.

As used herein, the term "type IIS" refers to a restriction enzyme that cuts at a site remote from its recognition sequence. Such enzymes are known to cut at a distances from their recognition sites ranging from 0 to 20 base pairs.

It is preferred that the support is semi-solid.

Preferably, the semi-solid support is selected from the group that includes polyacrylamide, cellulose, polyamide (nylon) and cross-linked agarose, -dextran and -polyethylene glycol.

It is particularly preferred that amplifying of nucleic acid molecules of is performed by polymerase chain reaction (PCR).

Preferably, affixing of nucleic acid molecules to the support is performed using a covalent linker that is selected from the group that includes oxidized 3-methyl uridine, an acrylyl group and hexaethylene glycol. Additionally, Acrydite oligonucleotide primers may be covalently fixed within a polyacrylamide gel.

It is also contemplated that affixing of nucleic acid molecules to the support is performed via hybridization of the members of the pool to nucleic acid molecules that are covalently bound to the support.

As used herein, the term synthetic oligonucleotide refers to a short (10 to 1,000 nucleotides in length), double- or single-stranded nucleic acid molecule that is chemically synthesized or is the product of a biological system such as a product of primed or unprimed enzymatic synthesis.

DETAILED DESCRIPTION OF THE INVENTION

The present invention is directed to the synthesis of nucleic acid array chips, methods by which such chips may be reproduced and methods by which they may be used in diverse applications relating to nucleic acid replication or amplification, genomic characterization, gene expression studies, medical diagnostics and population genetics. The nucleic acid array chips of the replica array has several advantages over the presently available methods.

Besides any known sequences or combinatorial sequence thereof, a full genome including unknown DNA sequences can be replicated according to the present invention. The size of the nucleic acid fragments or primers to be replicated can be from about 25-mer to about 9000-mer. The present invention is also quick and cost effective. It takes about only about one week from discovery of an organism to arrange the full genome sequence of the organism onto chips with about $10 per chip. In addition, the thickness of the chips is 3000 nm which provides a much higher sensitivity. The chips are compatible with inexpensive in situ PCR devices, and can be reused as many as 100 times.

The invention provides for an advance over the arrays of Chetverin and Kramer (WO 93/17126), Chetverin and Chetverina, 1997 (U.S. Pat. No. 5,616,478), and others, in that a method is herein described by which to produce a random nucleic acid array both that is covalently linked to a support (therefore extensively reusable) and that permits one to fabricate high-fidelity copies of it without returning to the starting point of the process, thereby eliminating time-consuming, expensive steps and providing for reproducible results both when the copies of the array are made and when they are used. It is evident that this method is not obvious, despite its great utility. No mention of replica plating or printing of amplimers in this context appears to have been made in oligonucleotide array patents or papers. There is no method in the prior art for generating a set of nucleic acid arrays comprising the steps of covalently linking a pool of nucleic acid molecules to a support to form a random array, amplifying the nucleic acid molecules and subsequently replicating the array.

While reproducibility of manufacture and durability are not of significant concern in the making of arrays in which the nucleic acid molecules are chemically synthesized directly on the support, they are centrally important in cases in which the molecules of the array are of natural origin (for example, a sample of mRNA from an organism). Each nucleic acid sample obtained from a natural source constitutes a unique pool of molecules; these molecules are, themselves, uniquely distributed over the surface of the support, in that the original laying out of the pattern is random. By any prior art method, an array generated from simple, random deposition of a pool of nucleic acid molecules is irreproducible; however, a set of related arrays would be of great utility, since information derived from any one copy from the replicated set would increase the confidence in the identity and/or quality of data generated using the other members of the set.

The methods provided in the present invention basically consists of 5 steps: 1) providing a pool of nucleic acid molecules, 2) plating or other transfer of the pool onto a solid support, 3) in situ amplification, 4) replica printing of the amplified nucleic acids and 5) identification of features. Sets of arrays so produced, or members thereof, then may be put to any chip affinity readout use, some of which are summarized below. The production of a set of arrays according to the invention is described in Example 1. The following examples are provided for exemplification purposes only and are not intended to limit the scope of the invention which has been described in broad terms above.

EXAMPLE 1

Production of a Plurality of a Nucleic Acid Array According to the Invention

Step 1. Production Nucleic Acid Pool with Which to Construct an Array According to the Invention A pool or library of n-mers (n=20 to 9000) is made by any of several methods. The pool is either amplified (e.g. by PCR) or left unamplified. A suitable in vitro amplification "vector", for example, flanking PCR primer sequences or an in vivo plasmid, phage or viral vector from which amplified molecules are excised prior to use, is used. If necessary, random shearing or enzymatic cleavage of large nucleic acid molecules is used to generate the pools if the nucleic acid molecules are amplified, cleavage is performed either before or after amplification. Alternatively, a nucleic acid sample is random primed, for example with tagged 3' terminal hexamers followed by electrophoretic size-selection. The nucleic acid is selected from genomic, synthetic or cDNA sequences (Power, 1996, *J. Hosp. Infect.*, 34: 247–265; Welsh, et al., 1995, *Mutation Res.*, 338: 215–229). The copied or unamplified nucleic acid fragments resulting from any of the above procedures are, if desired, fractionated by size or affinity by a variety of methods including electrophoresis, sedimentation, and chromatography (possibly including elaborate, expensive procedures or limited-quantity resources since the subsequent inexpensive replication methods can justify such investment of effort).

Pools of nucleic acid molecules are, at this stage, applied directly to the support medium (see Step 2, below). Alternatively, they are cloned into nucleic acid vectors. For example, pools composed of fragments with inherent polarity, such as cDNA molecules, are directionally cloned into nucleic acid vectors that comprise, at the cloning site, oligonucleotide linkers that provide asymmetric flanking sequences to the fragments. Upon their subsequent removal via restriction with enzymes that cleave the vector outside both the cloned fragment and linker sequences, molecules with defined (and different) sequences at their two ends are generated. By denaturing these molecules and spreading them onto a semi-solid support to which is covalently bound oligonucleotides that are complementary to one preferred flanking linker, the orientation of each molecule in the array is determined relative to the surface of the support. Such a polar array is of use for in vitro transcription/translation of the array or any purpose for which directional uniformity is preferred.

In addition to the attachment of linker sequences to the molecules of the pool for use in directional attachment to the support, a restriction site or regulatory element (such as a promoter element, cap site or translational termination signal), is, if desired, joined with the members of the pool. The use of fragments with termini engineered to comprise useful restriction sites is described below in Example 6.

Step 2. Transfer of the Nucleic Acid Pool onto a Support Medium

The nucleic acid pool is diluted ("plated") out onto a semi-solid medium (such as a polyacrylamide gel) on a solid surface such as a glass slide such that amplifiable molecules are 0.1 to 100 micrometers apart. Sufficient spacing is maintained that features of the array do not contaminate one another during repeated rounds of amplification and replication. It is estimated that a molecule that is immobilized at one end can, at most, diffuse the distance of a single molecule length during each round of replication. Obviously, arrays of shorter molecules are plated at higher density than those comprising long molecules.

Immobilizing media that are of use according to the invention are physically stable and chemically inert under the conditions required for nucleic acid molecule deposition, amplification and the subsequent replication of the array. A useful support matrix withstands the rapid changes in- and extremes of temperature required for PCR and retains structural integrity under stress during the replica printing process. The support material permits enzymatic nucleic acid synthesis; if it is unknown whether a given substance will do so, it is tested empirically prior to any attempt at production of a set of arrays according to the invention. The support structure comprises a semi-solid (i.e. gelatinous) lattice or matrix, wherein the interstices or pores between lattice or matrix elements are filled with an aqueous or other liquid medium; typical pore (or 'sieve') sizes are in the range of 100 $\mu$m to 5 nm. Larger spaces between matrix elements are within tolerance limits, but the potential for diffusion of amplified products prior to their immobilization is increased. The semi-solid support is compressible, so that full surface-to-surface contact, essentially sufficient to form a seal between two supports, although that is not the object, may be achieved during replica printing. The support is prepared such that it is planar, or effectively so, for the purposes of printing; for example, an effectively planar support might be cylindrical, such that the nucleic acids of the array are distributed over its outer surface in order to contact other supports, which are either planar or cylindrical, by rolling one over the other. Lastly, a support materials of use according to the invention permits immobilizing (covalent linking) of nucleic acid features of an array to it by means enumerated below. Materials that satisfy these requirements comprise both organic and inorganic substances, and include, but are not limited to, polyacrylamide, cellulose and polyamide (nylon), as well as cross-linked agarose, dextran or polyethylene glycol.

Of the support media upon which the members of the pool of nucleic acid molecules may be anchored, one that is particularly preferred is a thin, polyacylamide gel on a glass support, such as a plate, slide or chip. A polyacrylamide sheet of this type is synthesized as follows:

Acrylamide and bis-acrylamide are mixed in a ratio that is designed to yield the degree of crosslinking between individual polymer strands (for example, a ratio of 38:2 is typical of sequencing gels) that results in the desired pore size when the overall percentage of the mixture used in the gel is adjusted to give the polyacrylamide sheet its required tensile properties. Polyacrylamide gel casting methods are well known in the art (see Sambrook et al., 1989, *Molecular Cloning. A Laboratory Manual.*, 2nd Edition, Cold Spring Harbor Laboratory Press, Cold Spring Harbor, N.Y.), and one of skill has no difficulty in making such adjustments. The gel sheet is cast between two rigid surfaces, at least one of which is the glass to which it will remain attached after;removal of the other. The casting surface that is to be removed after polymerization is complete is coated with a lubricant that will not inhibit gel polymerization; for this purpose, silane is commonly employed. A layer of silane is spread upon the surface under a fume hood and allowed to stand until nearly dry. Excess silane is then removed (wiped or, in the case of small objects, rinsed extensively) with ethanol. The glass surface which will remain in association with the gel sheet is treated with γ-methacryloxypropyltrimethoxysilane (Cat. No. M6514, Sigma; St. Louis, Mo.), often referred to as 'crosslink silane', prior to casting. The glass surface that will contact the gel is triply-coated with this agent. Each treatment of an area equal to 1200 cm$^2$ requires 125 µl of crosslink silane in 25 ml of ethanol. Immediately before this solution is spread over the glass surface, it is combined with a mixture of 750 µl water and 75 µl glacial acetic acid and shaken vigorously.

The ethanol solvent is allowed to evaporate between coatings (about 5 minutes under a fume hood) and, after the last coat has dried, excess crosslink silane is removed as completely as possible via extensive ethanol washes in order to prevent 'sandwiching' of the other support plate onto the gel. The plates are then assembled and the gel cast as desired.

The only operative constraint that determines the size of a gel that is of use according to the invention is the physical ability of one of skill in the art to cast such a gel. The casting of gels of up to one meter in length is, while cumbersome, a procedure well known to workers skilled in nucleic acid sequencing technology. A larger gel, if produced, is also of use according to the invention. An extremely small gel is cut from a larger whole after polymerization is complete.

Note that at least one procedure for casting a polyacrylamide gel with bioactive substances, such as enzymes, entrapped within its matrix is known in the art (O'Driscoll, 1976, Methods Enzymol., 44: 169–183); a similar protocol, using photo-crosslinkable polyethylene glycol resins, that permit entrapment of living cells in a gel matrix has also been documented (Nojima and Yamada, 1987, Methods Enzymol, 136: 380–394). Such methods are of use according to the invention. As mentioned below, whole cells are typically cast into agarose for the purpose of delivering intact chromosomal DNA into a matrix suitable for pulsed-field gel electrophoresis or to serve as a "lawn" of host cells that will support bacteriophage growth prior to the lifting of plaques according to the method of Benton and Davis (see Maniatis et al., 1982, *Molecular Cloning: A Laboratory Manual*, Cold Spring Harbor Laboratory Press, Cold Spring Harbor, N.Y.). In short, electrophoresis-grade agarose (e.g. Ultrapure; Life Technologies/Gibco-BRL; is dissolved in a physiological (isotonic) buffer and allowed to equilibrate to a temperature of 50° to 52° C. in a tube, bottle or flask. Cells are then added to the agarose and mixed thoroughly, but rapidly (if in a bottle or tube, by capping and inversion, if in a flask, by swirling), before the mixture is decanted or pipetted into a gel tray. If low-melting point agarose is used, it may be brought to a much lower temperature (down to approximately room temperature, depending upon the concentration of the agarose) prior to the addition of cells. This is desirable for some cell types; however, if electrophoresis is to follow cell lysis prior to covalent attachment of the molecules of the resultant nucleic acid pool to the support, it is performed under refrigeration, such as in a 4° to 10° C. 'cold' room.

Immobilization of nucleic acid molecules to the support matrix according to the invention is accomplished by any of several procedures. Direct immobilizing, as through use of 3'-terminal tags bearing chemical groups suitable for covalent linkage to the support, hybridization of single-stranded molecules of the pool of nucleic acid molecules to oligonucleotide primers already bound to the support or the spreading of the nucleic acid molecules on the support accompanied by the introduction of primers, added either before or after plating, that may be covalently linked to the support, may be performed. Where pre-immobilized primers are used, they are designed to capture a broad spectrum of sequence motifs (for example, all possible multimers of a given chain length, e.g. hexamers), nucleic acids with homology to a specific sequence or nucleic acids containing variations on a particular sequence motif. Alternatively, the primers encompass a synthetic molecular feature common to all members of the pool of nucleic acid molecules, such as a linker sequence (see above).

Oligonucleotide primers useful according to the invention are single-stranded DNA or RNA molecules that are hybridizable to a nucleic acid template to prime enzymatic synthesis of a second nucleic acid strand. The primer is complementary to a portion of a target molecule present in a pool of nucleic acid molecules used in the preparation of sets of arrays of the invention.

It is contemplated that such a molecule is prepared by synthetic methods, either chemical or enzymatic. Alternatively, such a molecule or a fragment thereof is naturally occurring, and is isolated from its natural source or purchased from a commercial supplier. Oligonucleotide primers are 6 to 100, and even up to 1,000, nucleotides in length, but ideally from 10 to 30 nucleotides, although oligonucleotides of different length are of use.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, *Nucleic Acids Res.* 12: 203, incorporated herein by reference. As a result, it is expected that a certain degree of mismatch at the priming site is tolerated. Such mismatch may be small, such as a mono-, di- or tri-nucleotide. Alternatively, it may encompass loops, which we define as regions in which mismatch encompasses an uninterrupted series of four or more nucleotides.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher $T_M$ than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are genererally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone.

Primers are designed with the above first four considerations in mind. While estimates of the relative merits of numerous sequences are made mentally, computer programs have been designed to assist in the evaluation of these several parameters and the optimization of primer sequences. Examples of such programs are "PrimerSelect" of the DNAStar™ software package (DNAStar, Inc.; Madison, Wis.) and OLIGO 4.0 (National Biosciences, Inc.). Once designed, 15, suitable oligonucleotides are prepared by a suitable method, e.g. the phosphoramidite method described by Beaucage and Carruthers (1981, *Tetrahedron Lett.*, 22: 1859–1862) or the triester method according to Matteucci et al. (1981, *J. Am. Chem. Soc.*, 103: 3185), both incorporated herein by reference, or by other chemical methods using either a commercial automated oligonucleotide synthesizer or VLSIPS™ technology.

Two means of crosslinking a nucleic acid molecule to a preferred support of the invention, a polyacrylamide gel sheet, will be discussed in some detail. The first (provided by Khrapko et al., 1996, U.S. Pat. No. 5,552,270) involves the 3' capping of nucleic acid molecules with 3-methyl uridine; using this method, the nucleic acid molecules of the libraries of the present invention are prepared so as to include this modified base at their 3' ends. In the cited protocol, an 8% polyacrylamide gel (30:1, acrylamide: bis-acrylamide) sheet 30 μm in thickness is cast and then exposed to 50% hydrazine at room temperature for 1 hour; such a gel is also of use according to the present invention. The matrix is then air dried to the extent that it will absorb a solution containing nucleic acid molecules, as described below. Nucleic acid molecules containing 3-methyl uridine at their 3' ends are oxidized with 1 mM sodium periodate ($NaIO_4$) for 10 minutes to 1 hour at room temperature, precipitated with 8 to 10 volumes of 2% $LiClO_4$ in acetone and dissolved in water at a concentration of 10 pmol/μl. This concentration is adjusted so that when the nucleic acid molecules are spread upon the support in a volume that covers its surface evenly, yet is efficiently (i.e. completely) absorbed by it, the density of nucleic acid molecules of the array falls within the range discussed above. The nucleic acid molecules are spread over the gel surface and the plates are placed in a humidified chamber for 4 hours. They are then dried for 0.5 hour at room temperature and washed in a buffer that is appropriate to their subsequent use. Alternatively, the gels are rinsed in water, re-dried and stored at −20° C. until needed. It is said that the overall yield of nucleic acid that is bound to the gel is 80% and that of these molecules, 98% are specifically linked through their oxidized 3' groups.

A second crosslinking moiety that is of use in attaching nucleic acid molecules covalently to a polyacrylamide sheet is a 5' acrylyl group, which is attached to the primers used in Example 6. Oligonucleotide primers bearing such a modified base at their 5' ends may be used according to the invention. In particular, such oligonucleotides are cast directly into the gel, such that the acrylyl group becomes an integral, covalently-bonded part of the polymerizing matrix. The 3' end of the primer remains unbound, so that it is free to interact with- and hybridize to a nucleic acid molecule of the pool and prime its enzymatic second-strand synthesis.

Alternatively, hexaethylene glycol is used to covalently link nucleic acid molecules to nylon or other support matrices (Adams and Kron, 1994, U.S. Pat. No. 5,641,658). In addition, nucleic acid molecules are crosslinked to nylon via irradiation with ultraviolet light. While the length of time for which a support is irradiated as well as the optimal distance from the ultraviolet source is calibrated with each instrument used, due to variations in wavelength and transmission strength, at least one irradiation device designed specifically for crosslinking of nucleic acid molecules to hybridization membranes is commercially available (Stratalinker; Stratagene). It should be noted that in the process of crosslinking via irradiation, limited nicking of nucleic acid strand occurs; however, the amount of nicking is generally negligible under conditions such as those used in hybridization procedures. Attachment of nucleic acid molecules to the support at positions that are neither 5'- nor 3'-terminal also occurs, but it should be noted that the potential for utility of an array so crosslinked is largely uncompromised, as such crosslinking does not inhibit hybridization of oligonucleotide primers to the immobilized molecule where it is bonded to the support. The production of 'terminal' copies of an array of the invention, i.e. those that will not serve as templates for further replication, is not affected by the method of crosslinking; however, in situations in which sites of covalent linkage are, preferably, at the termini of molecules of the array, crosslinking methods other than ultraviolet irradiation are employed.

Step 3. Amplification of the Nucleic Acid Molecules of the Array

The molecules are amplified in situ (Tsongalis et al., 1994, *Clinical Chemistry*, 40: 381–384; see also review by Long and Komminoth, 1997, *Methods Mol. Biol.*, 71: 141–161) by standard molecular techniques, such as thermal-cycled PCR (Mullis and Faloona, 1987, *Methods Enzymol.*, 155: 335–350) or isothermal 3SR (Gingeras et al., 1990, *Annales de Biologie Clinique*, 48(7): 498–501; Guatelli et al., 1990, *Proc. Natl. Acad. Sci. U.S.A.*, 87: 1874). Another method of nucleic acid amplification that is of use according to the invention is the DNA ligase amplification reaction (LAR), which has been described as permitting the exponential increase of specific short sequences through the activities of any one of several bacterial DNA ligases (Wu and Wallace, 1989, *Genomics*, 4: 560). The contents of this article are herein incorporated by reference.

The polymerase chain reaction (PCR), which uses multiple cycles of DNA replication catalyzed by a thermostable, DNA-dependent DNA polymerase to amplify the target sequence of interest, is well known in the art, and is presented in detail in the Examples below. The second amplification process, 3SR, is an outgrowth of the transcription-based amplification system (TAS), which capitalizes on the high promoter sequence specificity and reiterative properties of bacteriophage DNA-dependent RNA polymerases to decrease the number of amplification cycles necessary to achieve high amplification levels (Kwoh et al., 1989, *Proc. Natl. Acad. Sci. U.S.A.*, 83: 1173–1177). The 3SR method comprises an isothermal, Self-Sustained Sequence Replication amplification reaction, is as follows:

Each priming oligonucleotide contains the T7 RNA polymerase binding sequence (TAATACGACTCACTATA [SEQ ID NO: 1]) and the preferred transcriptional initiation site. The remaining sequence of each primer is complementary to the target sequence on the molecule to be amplified.

The 3SR amplification reaction is carried out in 100 μl and contains the target RNA, 40 mM Tris.HCl, ph 8.1, 20 mM $MgCl2$, 2 mM spermidine.HCl, 5mM dithiothreitol, 80

μg/ml BSA, 1 mM dATP, 1 mM dGTP, 1 mM dTTP, 4 mMATP, 4 mM CTP, 1 mM GTP, 4 mM dTTP, 4 mM ATP, 4 mM CTP, 4 mM GTP, 4 mMUTP, and a suitable amount of oligonucleotide primer (250 ng of a 57-mer; this amount is scaled up or down, proportionally, depending upon the length of the primer sequence). Three to 6 attomoles of the nucleic acid target for the 3SR reactions is used. As a control for background, a 3SR reaction without any target ($H_2O$) is run. The reaction mixture is heated to 100° C. for 1 minute, and then rapidly chilled to 42° C. After 1 minute, 10 units (usually in a volume of approximately 2 μl) of reverse transcriptase, (e.g. avian myoblastosis virus reverse transcriptase, AMV-RT; Life Technologies/Gibco-BRL) is added. The reaction is incubated for 10 minutes, at 42° C. and then heated to 100° C. for 1 minute. (If a 3SR reaction is performed using a single-stranded template, the reaction mixture is heated instead to 65° C. for 1 minute.) Reactions are then cooled to 37 ° C. for 2 minutes prior to the addition of 4.6 μl of a 3SR enzyme mix, which contains 1.6 μl of AMV-RT at 18.5 units/μl, 1.0 μl T7 RNA polymerase (both e.g. from Stratagene; La Jolla, Calif.) at 100 units/μl and 2.0 μl E. Coli RNase H at 4 units/μl (e.g. from Gibco/Life Technologies; Gaithersburg, Md.). It is well within the knowledge of one of skill in the art to adjust enzyme volumes as needed to account for variations in the specific activities of enzymes drawn from different production lots or supplied by different manufacturers. The reaction is incubated at 37° C. for 1 hour and stopped by freezing. While the handling of reagents varies depending on the physical size of the array (which planar surface, if large, requires containment such as a tray or thermal-resistant hybridization bag rather than a tube), this method is of use to amplify the molecules of an array according to the invention.

Other methods which are of use in the amplification of molecules of the array include, but are not limited to, nucleic acid sequence-based amplification (NASBA; Compton, 1991, *Nature*, 350: 91–92, incorporated herein by reference) and strand-displacement amplification (SDA; Walker et al., 1992, *Nucleic Acids Res.*, 20: 1691–1696, incorporated herein by reference).

Step 1. Replication of the Array a. The master plate generated in steps 1 through 3 is replica-plated by any of a number of methods (reviewed by Lederberg, 1989, *Genetics*, 121(3): 395–9) onto similar gel-chips. This replica is performed by directly contacting the compressible surfaces of the two gels face to face with sufficient pressure that a few molecules of each clone are transferred from the master to the replica. Such contact is brief, on the order of 1 second to 2 minutes. This is done for additional replicas from the same master, limited only by the number of molecules post-amplification available for transfer divided by the minimum number of molecules that must be transferred to achieve an acceptably faithful copy. While it is theoretically possible to transfer as little as a single molecule per feature, a more conservative approach is taken. The number of each species of molecule available for transfer never approaches a value so low as to raise concern about the probability of feature loss or to the point at which a base substitution during replication of one member of a feature could, in subsequent rounds of amplification, create a significant (detectable) population of mutated molecules that might be mistaken for the unaltered sequence, unless errors of those types are within the limits of tolerance for the application for which the array is intended. Note that differential replicative efficiencies of the molecules of the array are not as great a concern as they would be in in the case of amplification of a conventional library, such as a phage library, in solution or on a non-covalently-bound array. Because of the physical limitations on diffusion of molecules of any feature, one which is efficiently amplified cannot 'overgrow' one which is copied less efficiently, although the density of complete molecules of the latter on the array may be low. It is estimated that 10 to 100 molecules per feature are sufficient to achieve fidelity during the printing process. Typically, at least 100 to 1000 molecules are transferred.

Alternatively, the plated DNA is reproduced inexpensively by microcontact printing, or μCP, (Jackman et al, 1995, *Science*, 269(5224): 664–666, 1995) onto a surface with an initially uniform (or patterned) coating of two oligonucleotides (one or both immobilized by their 5' ends) suitable for in situ amplification. Pattern elements are transferred from an elastomeric support (comparable in its physical properties to support materials that are useful according to the invention) to a rigid, curved object that is rolled over it; if desired, a further, secondary transfer of the pattern elements from the rigid cylinder or other object onto a support is performed. The surface of one or both is compliant to achieve uniform contact. For example, 30 micron thin polyacrylamide films are used for immobilizing oligomers covalently as well as for in situ hybridizations (Khrapko, et al., 1991, *DNA Sequence*, 1(6):375–88). Effective contact achieved with the transfer of very: few molecules of double- or single-stranded DNA from each sub-feature to the corresponding point on the recipient support.

b. The replicas are then amplified as in step 3.

c. Alternatively, a replica serves as a master for subsequent steps like step 4, limited by the diffusion of the features and the desired feature resolution.

Step 5. Identification of Features of the Array

Ideally, feature identification is performed on the first array of a set produced by the methods described above; however, it is also done using any array of a set, regardless of its position in the line of production. The features are sequenced by hybridization to fluorescently labeled oligomers representing all sequences of a certain length (.e.g. all 4096 hexamers) as described for Sequencing-by-Hybridization (SBH, also called Sequencing-by-Hybridization-to-an-Oligonucleotide-Matrix, or SHOM; Drmanac et al., 1993, *Science*, 260(5114): 1649–52; Khrapko, et al. 1991, supra; Mugasimangalam et al., 1997, *Nucleic Acids Res.*, 25: 800–805). The sequencing in step 5 is considerably easier than conventional SBH if the feature lengths are short (e.g. ss-25-mers rather than the greater than ds-300-mers used in SBH), if the genome sequence is known or if a preselection of features is used.

SBH involves a strategy of overlapping block reading. It is based on hybridization of DNA with the complete set of immobilized oligonucleotides of a certain length fixed in specific positions on a support. The efficiency of SBH depends on the ability to sort out effectively perfect duplexes from those that are imperfect (i.e. contain base pair mismatches). This is achieved by comparing the temperature-dependent dissociation curves of the duplexes formed by DNA and each of the immobilized oligonucleotides with standard dissociation curves for perfect oligonucleotide duplexes.

To generate a hybridization and dissociation curve, a $^{32}$P-labeled DNA fragment (30,000 cpm, 30 fmoles) in 1 μl of hybridization buffer (1M NaCl; 10 mM Na phosphate, pH 7.0; 0.5 mM EDTA) is pipetted onto a dry plate so as to cover a dot of an immobilized oligonucleotide. Hybridization is performed for 30 minutes at 0° C. The support is rinsed with 20 ml of hybridization buffer at 0° C. and then washed 10 times with the same buffer, each wash being performed for 1 minute at a temperature 5° C. higher than the previous one. The remaining radioactivity is measured after each wash with a minimonitor (e.g. a Mini monitor 125; Victoreen) additionally equipped with a count integrator, through a 5 mm aperture in a lead screen. The remaining radioactivity (% of input) is plotted on a logarithmic scale against wash temperature.

For hybridization with a fluorescently-labeled probe, a volume of hybridization solution sufficient to cover the array is used, containing the probe fragment at a concentration of 2 fmoles/0.01 µl. The hybridization incubated for 5.0 hour at 17° C. and then washed at 0° C., also in hybridization buffer. Hybridized signal is observed and photographed with a fluorescence microscope (e.g. Leitz "Aristoplan"; input filter 510–560 nm, output filter 580 nm) equipped with a photocamera. Using 250 ASA film, an exposure of approximately 3 minutes is taken.

For SBH, one suitable immobilization support is a 30 µm-thick polyacrylamide gel covalently attached to glass. Oligonucleotides to be used as probes in this procedure are chemically synthesized (e.g. by the solid-support phosphoramidite method, deprotected in ammonium hydroxide for 12 h at 55° C. and purified by PAGE under denaturing conditions). Prior to use, primers are labeled either at the 5'-end with [$\gamma$-$^{32}$P]ATP, using T4 polynucleotide kinase, to a specific activity of about 1000 cpm/fmol, or at the 3'-end with a fluorescent label, e.g. tetramethylrhodamine (TMR), coupled to dUTP through the base by terminal transferase (Aleksandrova et al., 1990, *Molek. Biologia* [*Moscow*], 24: 1100–1108) and further purified by PAGE.

An alternative method of sequencing involves subsequent rounds of stepwise ligation and cleavage of a labeled probe to a target polynucleotide whose sequence is to be determined (Brenner, U.S. Pat. No. 5,599,675). According to this method, the nucleic acid to be sequenced is prepared as a double-stranded DNA molecule with a "sticky end", in other words, a single-stranded terminal overhang, which overhang is of a known length that is uniform among the molecules of the preparation, typically 4 to 6 bases. These molecules are then probed in order to determine the identity of a particular base present in the single-stranded region, typically the terminal base. A probe of use in this method is a double-stranded polynucleotide which (i) contains a recognition site for a nuclease, and (ii) typically has a protruding strand capable of forming a duplex with a complementary protruding strand of the target polynucleotide. In each sequencing cycle, only those probes whose protruding strands form perfectly-matched duplexes with the protruding strand of the target polynucleotide hybridize- and are then ligated to the end of the target polynucleotide. The probe molecules are divided into four populations, wherein each such population comprises one of the four possible nucleotides at the position to be determined, each labeled with a distinct fluorescent dye. The remaining positions of the duplex-forming region are occupied with randomized, unlabeled bases, so that every possible multimer the length of that region is represented; therefore, a certain percentage of probe molecules in each pool are complementary to the single-stranded region of the target polynucleotide; however, only one pool bears labeled probe molecules that will hybridize.

After removal of the unligated probe, a nuclease recognizing the probe cuts the ligated complex at a site one or more nucleotides from the ligation site along the target polynucleotide leaving an end, usually a protruding strand, capable of participating in the next cycle of ligation and cleavage. An important feature of the nuclease is that its recognition site be separate from its cleavage site. In the course of such cycles of ligation and cleavage, the terminal nucleotides of the target polynucleotide are identified. As stated above, one such category of enzyme is that of type IIs restriction enzymes, which cleave sites up to 20 base pairs remote from their recognition sites; it is contemplated that such enzymes may exist which cleave at distances of up to 30 base pairs from their recognition sites.

Ideally, it is the terminal base whose identity is being determined (in which it is the base closest to the double-stranded region of the probe which is labeled), and only this base is cleaved away by the type IIs enzyme. The cleaved probe molecules are recovered (e.g. by hybridization to a complementary sequence immobilized on a bead or other support matrix) and their fluorescent emission spectrum measured using a fluorimeter or other light-gathering device.

Note that fluorimetric analysis may be made prior to cleavage of the probe from the test molecule; however, cleavage prior to qualitative analysis of fluorescence allows the next round of sequencing to commence while determination of the identity of the first sequenced base is in progress. Detection prior to cleavage is preferred where sequencing is carried out in parallel on a plurality of sequences (either segments of a single target polynucleotide or a plurality of altogether different target polynucleotides), e.g. attached to separate magnetic beads, or other types of solid phase supports, such as the replicable arrays of the invention. Note that whenever natural protein endonucleases are employed as the nuclease, the method further includes a step of methylating the target polynucleotide at the start of a sequencing operation to prevent spurious cleavages at internal recognition sites fortuitously located in the target polynucleotide.

By this method, there is no requirement for the electrophoretic separation of closely-sized DNA fragments, for difficult-to-automate gel-based separations, or the generation of nested deletions of the target polynucleotide. In addition, detection and analysis are greatly simplified because signal-to noise ratios are much more favorable on a nucleotide-by-nucleotide basis, permitting smaller sample sizes to be employed. For fluorescent-based detection schemes, analysis is further simplified because fluorophores labeling different nucleotides may be separately detected in homogeneous solutions rather than in spatially overlapping bands.

As alluded to, the target polynucleotide may be anchored to a solid-phase support, such as a magnetic particle, polymeric microsphere, filter material, or the like, which permits the sequential application of reagents without complicated and time-consuming purification steps. The length of the target polynucleotide can vary widely; however, for convenience of preparation, lengths employed in conventional sequencing are preferred. For example, lengths in the range of a few hundred basepairs, 200–300, to 1 to 2 kilobase pairs are most often used.

Probes of use in the procedure may be labeled in a variety of ways, including the direct or indirect attachment of radioactive moieties, fluorescent moieties, calorimetric moieties, and the like. Many comprehensive reviews of methodologies for labeling DNA and constructing DNA probes provide guidance applicable to constructing probes (see Matthews et al., 1988, *Anal. Biochem.*, 169: 1–25; Haugland, 1992, *Handbook of Fluorescent Probes and Research Chemicals*, Molecular Probes, Inc., Eugene, OR; Keller and Manak, 1993, *DNA Probes, 2nd Ed.*, Stockton Press, New York; Eckstein, ed., 1991, *Oligonucleotides and Analogues: A Practical Approach*, ML Press, Oxford, 1991);

Wetmur, 1991, *Critical Reviews in Biochemistry and Molecular Biology*, 26: 227–259). Many more particular labelling methodologies are known in the art (see Connolly, 1987, *Nucleic Acids Res.*, 15: 3131–3139; Gibson et al. 1987, *Nucleic Acids Res.*, 15: 5455–6467; Spoat et al., 1987, *Nucleic Acids Res.*, 15: 4837–4848; Fung et al., U.S. Pat. No. 4,757,141; Hobbs, et al., U.S. Pat. No. 5,151,507; Cruickshank, U.S. Pat. No. 5,091,519; [synthesis of functionalized oligonucleotides for attachment of reporter groups]; Jablonski et al., 1986, *Nucleic Acids Res.*, 14: 6115–6128 [enzyme/oligonucleotide conjugates]; and Urdea et al., U.S. Pat. No. 5,124,246 [branched DNA]). The choice of attachment sites of labeling moieties does not significantly affect the ability of a given labeled probe to identify nucleotides in the target polynucleotide, provided that such labels do not interfere with the ligation and cleavage steps. In particular, dyes may be conveniently attached to the end of the probe distal to the target polynucleotide on either the 3' or 5' termini of strands making up the probe, e.g. Eckstein (cited above), Fung (cited above), and the like. In some cases, attaching labeling moieties to interior bases or internucleoside linkages may be desirable.

As stated above, four sets of mixed probes are provided for addition to the target polynucleotide, where each is labeled with a distinguishable label. Typically, the probes are labeled with one or more fluorescent dyes, e.g. as disclosed by Menchen et al, U.S. Pat No. 5,188,934; Begot et al PCT application PCT/US90/05565. Each of four spectrally resolvable fluorescent labels may be attached, for example, by way of Aminolinker II (all available from Applied Biosystems, Inc., Foster City, Calif.); these include TAMRA (tetramethylrhodamine), FAM (fluorescein), ROX (rhodamine X), and JOE (2', 7'-dimethoxy-4', 5'-dichlorofluorescein) and their attachment to oligonucleotides is described in Fung et al., U.S. Pat. No. 4,855,225.

Typically, nucleases employed in the invention are natural protein endonucleases (i) whose recognition site is separate from its cleavage site and (ii) whose cleavage results in a protruding strand on the target polynucleotide. Class IIS restriction endonucleases that may be employed are as previously described (Szybalski et al., 1991, *Gene*, 100: 13–26; Roberts et al., 1993, *Nucleic Acids Res.*, 21: 3125–3137; Livak and Brenner, U.S. Pat No. 5,093,245). Exemplary class IIs nucleases include AlwXI, BsmAI, BbvI, BsmFI, SisI, HgaI, BscAI, BbvII, BcefI, Bce85I, BccI, BcgI, BsaI, BsgI, BspMI, Bst71 I, EarI, Eco57I, Esp3I, FauI, FokI, GsuI, HphI, MboII, MmeI, RleAI, SapI, SfaNI, TaqII, Tth111II, Bco5I, BpuAI, FinI, BsrDI, and isoschizomers thereof. Preferred nucleases include Fok1, HgaI, EarI, and SfaNI. Reactions are generally carried out in 50 µL volumes of manufacturer's (New England Biolabs) recommended buffers for the enzymes employed, unless otherwise indicated. Standard buffers are also described in Sambrook et al., 1989, supra.

When conventional ligases are employed, the 5' end of the probe may be phosphorylated. A 5' monophosphate can be attached to a second oligonucleotide either chemically or enzymatically with a kinase (see Sambrook et al., 1989, supra). Chemical phosphorylation is described by Horn and Urdea, 1986, *Tetrahedron Lett.*, 27: 4705, and reagents for carrying out the disclosed protocols are commercially available (e.g. 51 Phosphate-ONTm from Clontech Laboratories; Palo Alto, Calif.).

Chemical ligation methods are well known in the art, e.g. Ferris et al., 1989, *Nucleosides & Nuleotides*, 8: 407–414; Shabarova et al., 1991, *Nucleic Acids Res.*, 19: 4247–4251. Typically, ligation is carried out enzymatically using a ligase in a standard protocol. Many ligases are known and are suitable for use in the invention (Lehman, 1974, *Science*, 186: 790–797; Engler et al., 1982, "DNA Ligases", in Boyer, ed., *The Enzymes Vol.* 15B pp. 3–30, Academic Press, New York). Preferred ligases include T4 DNA ligase, T7 DNA ligase, *E. Coli* DNA ligase, Taq ligase, Pfu ligase and Tth ligase. Protocols for their use are well known, (e.g. Sambrook et al., 1989, supra; Barany, 1991, *PCR Methods and Applicatios*, 1: 5–16; Marsh et al., 1992, Strategies, 5: 73–76). Generally, ligases require that a 5' phosphate group be present for ligation to the 3' hydroxyl of an abutting strand. This is conveniently provided for at least one strand of the target polynucleotide by selecting a nuclease which leaves a 5' phosphate, e.g. FokI.

Prior to nuclease cleavage steps, usually at the start of a sequencing operation, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the so-called "cognate" methylase of the nuclease being used; for most (if not all) type II bacterial restriction endonucleases, there exist cognate methylases that methylate their corresponding recognition sites. Many such methylases are known in the art (Roberts et al., 1993, supra; Nelson et al., 1993, *Nucleic Acids Res.*, 21: 3139–3154) and are commercially available from a variety of sources, particularly New England Biolabs (Beverly, Mass.).

The method includes an optional capping step after the unligated probe is washed from the target polynucleotide. In a capping step, by analogy with polynucleotide synthesis (e.g. Andrus et al., U.S. Pat. No. 4,816,571), target polynucleotides that have not undergone ligation to a probe are rendered inert to further ligation steps in subsequent cycles. In this manner spurious signals from "out of phase" cleavages are prevented. When a nuclease leaves a 5' protruding strand on the target polynucleotides, capping is usually accomplished by exposing the unreacted target polynucleotides to a mixture of the four dideoxynucleoside triphosphates, or other chain-terminating nucleoside triphosphates, and a DNA polymerase. The DNA polymerase extends the Y strand of the unreacted target polynucleotide by one chain-terminating nucleotide, e.g. a dideoxynucleotide, thereby rendering it incapable of ligating with probe in subsequent cycles.

Alternatively, a simple method involving quantitative incremental fluorescent nucleotide addition sequencing (QIFNAS), is employed in which each end of each clonal oligonucleotide is sequenced by primer extension with a nucleic acid polymerase (e.g. Klenow or Sequenase™;

U.S. Biochemicals) and one nucleotide at a time which has a traceable level of the corresponding fluorescent dNTP or rNTP, for example, 100 micromolar dCTP and 1 micromolar fluorescein-dCTP. This is done sequentially, e.g. dATP, dCTP, dGTP, dTTP, dATP and so forth until the incremental change in fluorescence is below a percentage that is adequate for useful discrimination from the cumulative total from previous cycles. The length of the sequence so determined may be extended by any of periodic photobleaching or cleavage of the accumulated fluorescent label from nascent nucleic acid molecules or denaturing the nascent nucleic acid strands from the array and re-priming the synthesis using sequence already obtained.

After features are identified on a first array of the set, it is desirable to provide landmarks by which subsequently-produced arrays of the set are aligned with it, thereby enabling workers to locate on them features of interest. This is important, as the first array of a set produced by the method of the invention is, by nature, random, in that the nucleic acid molecules of the starting pool are not placed down in a specific or pre-ordered pattern based upon knowledge of their sequences.

Several types of markings are made according to the technology available in the art. For instance, selected features are removed by laser ablation (Matsuda and Chung 1994, *ASAIQ Journal*, 40(3): M594–7; Jay, 1988, *Proc. Natl. Acad. Sci. U.S.A.*, 85: 5454–5458; Kimble, 1981, *Dev. Biol.*, 87(2): 286–300) or selectively replicated on copies of an array by laser-enhanced adhesion (Emmert-Buck et al, 1996, *Science*, 274(5289): 998–1001). These methods are used to eliminate nucleic acid features that interfere with adjacent features or to create a pattern that is easier for software to align.

Laser ablation is carried out as follows: A KrF excimer laser, e.g. a Hamamatsu L4500 (Hamamatsu, Japan) (pulse wavelength, 248 nm; pulse width, 20 ns) is used as the light source. The laser beam is converged through a laser-grade UV quartz condenser lens to yield maximum fluences of 3.08 $J/cm^2$ per pulse. Ablation of the matrix and underlying glass surface is achieved by this method. The depth of etching into the glass surfaces is determined using real-time scanning laser microscopy (Lasertec 1LM21W, Yokohama, Japan), and a depth profile is determined.

Selective transfer of features via laser-capture microdissection proceeds as follows: A flat film (100 $\mu$m thick) is made by spreading a molten thermoplastic material e.g. ethylene vinyl acetate polymer (EVA; Adhesive Technologies; Hampton, N.H.) on a smooth silicone or polytetrafluoroethylene surface. The optically-transparent thin film is placed on top of an array of the invention, and the array/film sandwich is viewed in an inverted microscope (e.g. and Olympus Model CK2; Tokyo) at 10×magnification (10× objective). A pulsed carbon dioxide laser beam is introduced by way of a small front-surface mirror coaxial with the condenser optical path, so as to irradiate the upper surface of the EVA film. The carbon dioxide laser (either Apollo Company model 580, Los Angeles, or California Laser Company model LS150, San Marcos, Calif.) provides individual energy pulses of adjustable length and power. A ZnSe lens focuses the laser beam to a target of adjustable spot size on the array. For transfer spots of 150 $\mu$m diameter, a 600-microsecond pulse delivers 25–30 mW to the film. The power is decreased or increased approximately in proportion to the diameter of the laser spot focused on the array. The absorption coefficient of the EVA film, measured by Fourier transmission, is 200 $cm^{-1}$ at a laser wavelength of 10.6 $\mu$m. Because >90% of the laser radiation is absorbed within the thermoplastic film, little direct heating occurs. The glass plate or chip upon which the semi-solid support has been deposited provides a heat sink that confines the full-thickness transient focal melting of the thermoplastic material to the targeted region of the array. The focally-molten plastic moistens the targeted tissue. After cooling and recrystallization, the film forms a local surface bond to the targeted nucleic acid molecules that is stronger than the adhesion forces that mediate their affinity for the semi-solid support medium. The film and targeted nucleic acids are removed from the array, resulting in focal microtransfer of the targeted nucleic acids to the film surface.

If removal of molecules from the array by this method is performed for the purpose of ablation, the procedure is complete. If desired, these molecules instead are amplified and cloned out, as described in Example 7.

A method provided by the invention for the easy orientation of the nucleic acid molecules of a set of arrays relative to one another is "array templating". A homogeneous solution of an initial library of single-stranded DNA molecules is spread over a photolithographic all-10-mer ss-DNA oligomer array under conditions which allow sequences comprised by library members to become hybridized to member molecules of the array, forming an arrayed library where the coordinates are in order of sequence as defined by the array. For example, a 3'-immobilized 10-mer (upper strand), binds a 25-mer library member (lower strand) as shown below:

5'-TGCATGCTAT-3'[SEQ ID NO: 2]

3'-CGATGCATTTACGTAACGTACGATA-5'[SEQ ID NO: 3]

Covalent linkage of the 25-mer sequence to the support, amplification and replica printing are performed by any of the methods described above. Further characterization, if required, is carried out by SBH, fluorescent dNTP extension or any other sequencing method applicable to nucleic acid arrays, such as are known in the art. This greatly enhances the ability to identify the sequence of a sufficient number of oligomer features in the replicated array to make the array useful in subsequent applications.

EXAMPLE 2

Ordered Chromosomal Arrays According to the Invention

Direct in situ single-copy (DISC)-PCR is a method that uses two primers that define unique sequences for on-slide PCR directly on metaphase chromosomes (Troyer et al., 1994a, *Mammalian Genoime*, 5: 112–114; summarized by Troyer et al., 1997, *Methods Mol. Biol., Vol. 71: PRINS and In Situ PCR Protocols*, J. R. Godsen, ed., Humana Press, Inc., Totowa, N.J., pp. 71–76). It thus allows exponential accumulation of PCR product at specific sites, and so may be adapted for use according to the invention.

The DISC-PCR procedure has been used to localize sequences as short as 100–300bp to mammalian chromosomes (Troyer et al., 1994a, supra; Troyer et al., 1994b, *Cytogenet. Cell Genetics*, 67(3), 199–204; Troyer et al., 1995, *Anim. Biotechnology*, 6(1): 51–58; and Xie et al., 1995, *Mammalian Genome* 6: 139–141). It is particularly suited for physically assigning sequence tagged sites (STSs), such as microsatellites (Litt and Luty, 1989, *Am. J. Hum. Genet.*, 44: 397–401; Weber and May, 1989, *Am. J. Hum. Genet* 44, 338–396), many of which cannot be assigned by in situ hybridization because they have been isolated from small-insert libraries for rapid sequencing. It can also be utilized to map expressed sequence tags (ESTs) physically (Troyer, 1994a, supra; Schmutz et al., 1996, *Cytogenet. Cell Genetics*, 72: 37–39). DISC-PCR obviates the necessity for an investigator to have a cloned gene in hand, since all that is necessary is to have enough sequence information to synthesize PCR primers. By the methods of the invention, target-specific primers need not even be utilized; all that is required is a mixed pool of primers whose members have at one end a 'universal' sequence, suitable for manipulations such as restriction endonuclease cleavage or hybridization to oligonucleotide molecules immobilized on- or added to a semi-solid support and, at the other end, an assortment of random sequences (for example, every possible hexamer)

which will prime in situ amplification of the chromosome. As described above, the primers may include terminal crosslinking groups with which they may be attached to the semi-solid support of the array following transfer; alternatively, they may lack such an element, and be immobilized to the support either through ultraviolet crosslinking or through hybridization to complementary, immobilized primers and subsequent primer extension, such that the newly-synthesized strand becomes permanently bound to the array. The DISC-PCR procedure is summarized briefly as follows:

Metaphase chromosomes anchored to glass slides are prepared by standard techniques (Halnan, 1989, in Cytogenetics of Animals, C. R. E. Halnan, ed., CAB International, Wallingford, U.K., pp. 451–456; ), using slides that have been pre-rinsed in ethanol and dried using lint-free gauze. Slides bearing chromosome spreads are washed in phosphate-buffered saline (PBS; 8.0 g NaCl, 1.3 g $Na_2HPO_4$ and 4 g $NaH_2PO_4$ dissolved in deionized water, adjusted to a volume of 1 liter and pH of 7.4) for 10 min and dehydrated through an ethanol series (70-, 80-, 95-, and 100%). Note that in some cases, overnight fixation of chromosomes in neutral-buffered formalin followed by digestion for 15 minutes with pepsinogen (2 mg/ml; Sigma) improves amplification efficiency.

For each slide, the following solution is prepared in a microfuge tube: 200 $\mu$M each dATP, dCTP, dGTP and dTTP; all deoxynucleotides are maintained as frozen, buffered 10 mM stock solutions or in dry form, and may be obtained either in dry or in solution from numerous suppliers (e.g. Perkin Elmer, Norwalk, CT; Sigma, St. Louis, Mo.; Pharmacia, Uppsala, Sweden). The reaction mixture for each slide includes 1.5 $\mu$M each primer (from 20 $\mu$M stocks), 2.0 $\mu$l 10×Taq polymerase buffer (100 mM Tris-HCl, pH 8.3, 500 mM KCl, 15 mM $MgCl_2$, 0.1% BSA; Perkin Elmer), 2.5 units AmpliTaq polymerase (Perkin Elmer) and deionzed $H_2O$ to a final volume of 20 $\mu$l. Note that the commercially supplied Taq polymerase buffer is normally adequate; however, adjustments may be made as needed in [$MgCl_2$] or pH, in which case an optimization kit, such as the OptiPrimer PCR Kit (Stratagene; La Jolla, Calif.) may be used. The above reaction mixture is pipetted onto the metaphase chromosomes and covered with a 22×50 mm coverslip, the perimeter of which is then sealed with clear nail polish. All air bubbles, even the smallest, are removed prior to sealing, as they expand when heated, and will inhibit the reaction. A particularly preferred polish is Hard As Nails (Sally Hansen); this nail enamel has been found to be resistant to leakage, which, if it occurred, would also compromise the integrity of the reaction conditions and inhibit amplification of the chromosomal DNA sequences. One heavy coat is sufficient. After the polish has been allowed to dry at room temperature, the edges of the slide are covered with silicone grease (Dow Corning Corporation, Midland, Mich.). Slides are processed in a suitable thermal cycler (i.e. one designed for on-slide PCR, such as the BioOven III; Biotherm Corp., Fairfax, Va.) using the following profile:

a. 94° C. for 3 min.
b. Annealing temperature of primers for 1 min.
c. 72° C. for 1 min.
d. 92° C. for 1 min.
e. Cycle to step b 24: more times (25 cycles total).
f. Final extension step of 3–5 min.

After thermal cycling is complete, silicone grease is removed with a tissue, and the slide is immersed in 100% ethanol. Using a sharp razor blade, the nail polish is cut through and the edge of the coverslip is lifted gently and removed. It is critical that the slide never be allowed to dry from this point on, although excess buffer is blotted gently off of the slide edge. The slide is immersed quickly in 4×SSC and excess nail polish is scraped from the edges of the slide prior to subsequent use.

The slide is contacted immediately with a semi-solid support in order to transfer to it the amplified nucleic acid molecules; alternatively, that the slide is first equilibrated in a liquid medium that is isotonic with- or, ideally, identical to that which permeates (i.e. is present in the pores of-) the semi-solid support matrix. From that point on, the array is handled comparably with those prepared according to the methods presented in Example 1. Feature identification, also as described above, permits determination of the approximate positions of genetic elements along the length of the template chromosome. In preparations in which chromosomes are linearly extended (stretched), the accuracy of gene ordering is enhanced. This is particularly useful in instances in which such information is not known, either through classical or molecular genetic studies, even in the extreme case of a chromosome that is entirely uncharacterized. By this method, comparative studies of homologous chromosomes between species of interest are performed, even if no previous genetic mapping has been performed on either. The information so gained is valuable in terms of gauging the evolutionary relationships between species, in that both large and small chromosomal rearrangements are revealed. The genetic basis of phenotypic differences between different individuals of a single species, e.g. human subjects, is also investigated by this method. When template chromosomes are condensed (coiled), more information is gained regarding the in vivo spatial relationships among genetic elements. This may have implications in terms of cell-type specific gene transcriptional activity, upon which comparison of arrays generated from samples comprising condensed chromosomes drawn from cells of different tissues of the same organism may shed light.

While the methods by which histological samples are prepared, PCR is performed and the first copy of the chromosomal array is generated are time-consuming, multiple copies of the array are produced easily according to the invention, as described above in Example 1 and elsewhere. The ability of the invention to reproduce what would, otherwise, be a unique array provides a valuable tool by which scientists have the power to work in parallel- or perform analyses of different types upon comparable samples. In addition, it allows for the generation of still more copies of the array for distribution to any number of other workers who may desire to confirm or extend any data set derived from such an array at any time.

A variation on this use of the present invention is chromosome templating. DNA (e.g. that of a whole chromosome) is stretched out and fixed on, a surface (Zimmermann and Cox, 1994, *Nucleic Acids Res.*, 22(3): 492–497). Segments of such immobilized DNA are made single-stranded by exonucleases, chemical denaturants (e.g. formamide) and/or heat. The single stranded regions are hybridized to the variable portions of an array of single-stranded DNA molecules each bearing regions of randomized sequence, thereby forming an array where the coordinates of features correspond to their order on a linear extended chromosome. Alternatively, a less extended structure, which replicates the folded or partially-unfolded state of various nucleic acid compartments in a cell, is made by using a condensed (coiled), rather than stretched, chromosome.

EXAMPLE 3

RNA Localization Arrays

The methods described in Example 2, above, are applied with equal success to the generation of an array that provides a two-dimensional representation of the spatial distribution of the RNA molecules of a cell. This method is applied to 'squashed' cellular material, prepared as per the chromosomal spreads described above in Example 2; alternatively, sectioned tissue samples affixed to glass surfaces are used. Either paraffin-, plastic- or frozen (Serrano et al., 1989, *Dev. Biol.* 132: 410–418) sections are used in the latter case.

Tissue samples are fixed using conventional reagents; formalin, 4% paraformaldehyde in an isotonic buffer, formaldehyde (each of which confers a measure of RNAase resistance to the nucleic acid molecules of the sample) or a multi-component fixative, such as FAAG (85% ethanol, 4% formaldehyde, 5% acetic acid, 1% EM grade glutaraldehyde) is adequate for this procedure. Note that water used in the preparation of any aqueous components of solutions to which the tissue is exposed until it is embedded is RNAase-free, i.e. treated with 0.1% diethylprocarbonate (DEPC) at room temperature overnight and subsequently autoclaved for 1.5 to 2 hours. Tissue is fixed at 4° C., either on a sample roller or a rocking platform, for t2 to 48 hours in order to allow fixative to reach the center of the sample. Prior to embedding, samples are purged of fixative and dehydrated; this is accomplished through a series of two- to ten-minute washes in increasingly high concentrations of ethanol, beginning at 60%- and ending with two washes in 95%- and another two in 100% ethanol, followed two ten-minute washes in xylene. Samples are embedded in any of a variety of sectioning supports, e.g. paraffin, plastic polymers or a mixed paraffin/polymer medium (e.g. Paraplast®Plus Tissue Embedding Medium, supplied by Oxford Labware). For example, fixed, dehydrated tissue is transferred from the second xylene wash to paraffin or a paraffin/polymer resin in the liquid-phase at about 58° C., then replace three to six times over a period of approximately three hours to dilute out residual xylene, followed by overnight incubation at 58° C. under a vacuum, in order to optimize infiltration of the embedding medium in to the tissue. The next day, following several more changes of medium at 20 minute to one hour intervals, also at 58° C., the tissue sample is positioned in a sectioning mold, the mold is surrounded by ice water and the medium is allowed to harden. Sections of 6 μm thickness are taken and affixed to 'subbed' slides, which are those coated with a proteinaceous substrate material, usually bovine serum albumin (BSA), to promote adhesion. Other methods of fixation and embedding are also applicable for use according to the methods of the invention; examples of these are found in Humason, G. L., 1979, *Animal Tissue Techniques*, 4th ed. (W.H. Freeman & Co., San Francisco), as is frozen sectioning.

Following preparation of either squashed or sectioned tissue, the RNA molecules of the sample are reverse-transcribed in situ. In order to contain the reaction on the slide, tissue sections are placed on a slide thermal cycler (e.g. Tempcycler II; COY Corp., Grass Lake, Mich.) with heating blocks designed to accommodate glass microscope slides. Stainless steel or glass (Bellco Glass Inc.; Vineland, N.J.) tissue culture cloning rings approximately 0.8 cm (inner diameter) X 1.0 cm in height are placed on top of the tissue section. Clear nail polish is used to seal the bottom of the ring to the tissue section, forming a vessel for the reverse transcription and subsequent localized in situ amplification (LISA) reaction (Tsongalis et al., 1994, supra).

Reverse transcription is carried out using reverse transcriptase, (e.g. avian myoblastosis virus reverse transcriptase, AMV-RT; Life Technologies/Gibco-BRL or Moloney Murine Leukemia Virus reverse transcriptase, M-MLV-RT, New England Biolabs, Beverly, Mass.) under the manufacturer's recommended reaction conditions. For example, the tissue sample is rehydrated in the reverse transcription reaction mix, minus enzyme, which contains 50 mM Tris.HCl (pH 8.3), 8 mM $MgCl_2$, 10 mM dithiothreitol, 1.0 mM each dATP, dTTP, dCTP and dGTP and 0.4 mM oligo-dT (12- to 18-mers). The tissue sample is, optionally, rehydrated in RNAase-free TE (10 mM Tris.HCl, pH 8.3 and 1 mM EDTA), then drained thoroughly prior to addition of the reaction buffer. To denature the RNA molecules, which may have formed some double-stranded secondary structures, and to facilitate primer annealing, the slide is heated to 65 ° C. for 1 minute, after which it is cooled rapidly to 37° C. After 2 minutes, 500 units of M-MLV-RT are added the mixture, bringing the total reaction volume to 100 μl. The reaction is incubated at 37° C. for one hour, with the reaction vessel covered by a microscope cover slip to prevent evaporation.

Following reverse transcription, reagents are pipetted out of the containment ring structure, which is rinsed thoroughly with TE buffer in preparation for amplification of the resulting cDNA molecules.

The amplification reaction is performed in a total volume of 25 μl, which consists of 75 ng of both the forward and reverse primers (for example the mixed primer pools 1 and 2 of Example 6) and 0.6 U of Taq polymerase in a reaction solution containing, per liter: 200 nmol of each deoxynucleotide triphosphate, 1.5 mmol of $MgCl_2$, 67 mmol of Tris.HCl (pH 8.8), 10 mmol of 2-mercaptoethanol, 16.6 mmol of ammonium sulfate, 6.7 μmol of EDTA, and 10 μmol of digoxigenin-11-dUTP. The reaction mixture is added to the center of the cloning ring, and layered over with mineral oil to prevent evaporation before slides are placed back onto the slide thermal cycler. DNA is denatured in situ at 94° C. for 2 min prior to amplification. LISA is accomplished by using 20 cycles, each consisting of a 1-minute primer annealing step (55° C.), a 1.5-min extension step (72° C.), and a 1-min denaturation step (94° C.). These amplification cycle profiles differ from those used in tube amplification to preserve optimal tissue morphology, hence the distribution of reverse transcripts and the products of their amplification on the slide.

Following amplification, the oil layer and reaction mix are removed from the tissue sample, which is then rinsed with xylene. The containment ring is removed with acetone, and the tissue containing the amplified cDNA is rehydrated by washing three times in approximately 0.5 ml of a buffer containing 100 mM Tris-Cl (pH 7.5) and 150 mM NaCl. The immobilized nucleic acid array of the invention is then formed by contacting the amplified nucleic acid molecules with a semi-solid support and covalently crosslinking them to it, by any of the methods described above.

Features are identified using SBH, also as described above, and correlated with the positions of mRNA molecules in the cell.

EXAMPLE 4

Size-sorted Genomic Arrays

As mentioned above, it is possible to prepare a support matrix in which are embedded whole, even living, cells. Such protocols have been developed for various purposes, such as encapsulated, implantable cell-based drug-delivery vehicles, and the delivery to an electophoretic matrix of very large, unsheared DNA molecules, as required for pulsed-field gel electrophoresis (Schwartz and Cantor, 1984, *Cell*, 37: 67–75). The arrays of the invention are constructed using as the starting material genomic DNA from a cell of an organism that has been embedded in an electrophoretic matrix and lysed in situ, such that intact nucleic acid molecules are released into the support matrix environment. If an array based upon copies of large molecules is made, such as is of use in a fashion similar to the chromosomal element ordering arrays described above in Example 2, then a low-percentage agarose gel is used as a support. Following lysis (Schwartz and Cantor, 1984, supra), the resulting large molecules may be size-sorted electrophoretically prior to in situ PCR amplification and linkage to the support, both as described above. If it is desired to preserve the array on a support other than agarose, which may be difficult to handle if the gel is large, the array is transferred via electroblotting onto a second support, such as a nylon or nitrocellulose membrane prior to linkage.

If it is not considered essential to preserve the associations between members of genetic linkage groups (at the coarsest level of resolution, chromosomes), nucleic acid molecules are cleaved, mechanically, chemically or enzymatically, prior to electrophoresis. A more even distribution of nucleic acid over the support results, and physical separation of individual elements from one another is improved. In such a case, a polyacrylamide, rather than agarose, gel matrix is used as a support. The arrays produced by this method do, to a certain extent, resemble sequencing gels; cleavage of an electrophoresed array, e.g. with a second restriction enzyme or combination thereof, followed by electrophoresis in a second dimension improves resolution of individual nucleic acid sequences from one another.

Such an array is constructed to any desired size. It is now feasible to scan large gels (for example, 40 cm in length) at high resolution. In addition, advances in gel technology now permit sequencing to be performed on gels a mere 4 cm long, one tenth the usual length, which demonstrates that a small gel is also useful according to the invention.

EXAMPLE 5
Spray-painted Arrays (Inkjet)

Immobilized nucleic acid molecules may, if desired, be produced using a device (e.g., any commercially-available inkjet printer, which may be used in substantially unmodified form) which sprays a focused burst of nucleic acid synthesis compounds onto a support (see Castellino, 1997, *Genome Res.*, 7: 943–976). Such a method is currently in practice at Incyte Pharmaceuticals and Rosetta Biosystems, Inc., the latter of which employs what are said to be minimally-modified Epson inkjet cartridges (Epson America, Inc.; Torrance, Calif.). The method of inkjet deposition depends upon the piezoelectric effect, whereby a narrow tube containing a liquid of interest (in this case, oligonucleotide synthesis reagents) is encircled by an adapter. An electric charge sent across the adapter causes the adapter to expand at a different rate than the tube, and forces a small drop of liquid containing phosphoramidite chemistry reagents from the tube onto a coated slide or other support.

Reagents are deposited onto a discrete region of the support, such that each region forms a feature of the array; the desired nucleic acid sequence is synthesized drop-by-drop at each position, as is true in other methods known in the art. If the angle of dispersion of reagents is narrow, it is possible to create an array comprising many features. Alternatively, if the spraying device is more broadly focused, such that it disperses nucleic acid synthesis reagents in a wider angle, as much as an entire support is covered each time, and an array is produced in which each member has the same sequence (i.e. the array has only a single feature).

Arrays of both types are of use in the invention; a multi-feature array produced by the inkjet method is used in array templating, as described above; a random library of nucleic acid molecules are spread upon such an array as a homogeneous solution comprising a mixed pool of nucleic acid molecules, by contacting the array with a tissue sample comprising nucleic acid molecules, or by contacting the array with another array, such as a chromosomal array (Example 2) or an RNA localization array (Example 3).

Alternatively, a single-feature array produced by the inkjet method is used by the same methods to immobilize nucleic acid molecules of a library which comprise a common sequence, whether a naturally-occurring sequence of interest (e.g. a regulatory motif) or an oligonucleotide primer sequence comprised by all or a subset of library members, as described herein above and in Example 6, below.

Nucleic acid molecules which thereby are immobilized upon an ordered inkjet array (whether such an array comprises one or a plurality of oligonucleotide features) are amplified in situ, transferred to a semi-solid support and immobilized thereon to form a first randomly-patterned, immobilized nucleic acid array, which is subsequently used as a template with which to produce a set of such arrays according to the invention, all as described above.

EXAMPLE 6
Isolation of a Feature from an Array of the Invention (Method 1)/Heterologous Arrays As described above in Example 1, sets of arrays are, if desired, produced according to the invention such that they incorporate oligonucleotide sequences bearing restriction sites linked to the ends of each feature. This provides a method for creating spatially-unique arrays of primer pairs for in situ amplification, in which each feature has a distinct set of primer pairs. One or both of the universal primers comprises a restriction endonuclease recognition site, such as a type IIS sequence (e.g. as Eco57I or MmeI which will cut up to 20 bp away). Treatment of the whole double-stranded array with the corresponding enzyme(s) followed by melting and washing away the non-immobilized strand creates the desired primer pairs with well-defined 3' ends. Alternatively, a double-strand-specific 3' exonuclease treatment of the double-stranded array is employed, but the resulting single-stranded 3' ends may vary in exact endpoint. The 3' end of the primers are used for in situ amplification, for example of variant sequences in diagnostics. This method, by which arrays of unique primer pairs are produced efficiently, provides an advance over the method of Adams and Kron (1997, supra), in which each single pair of primers is manually constructed and placed. Cloning of a given feature from an array of such a set is performed as follows:

MmeI is a restriction endonuclease having the property of cleaving at a site remote from its recognition site, TCCGAC. Heterogeneous pools of primers are constructed that comprise (from 5' to 3') a sequence shared by all members of the pool, the MmeI recognition site, and a variable region. The variable region may comprise either a fully-randomized sequence (e.g. all possible hexamers) or a selected pool of sequences (e.g. variations on a particular protein-binding, or other, functional sequence motif). If the variable sequence is random, the length of the randomized sequence determines the sequence complexity of the pool. For example, randomization of a hexameric sequence at the 3' ends of the primers results in a pool comprising 4,096 distinct sequence combinations. Examples of two such mixed populations of oligonucleotides (in this case, 32-mers) are primer pools 1s and 2s, below:

primer 1 (a pool of 4096 32-mers):
5' gcagcagtacgactagcataTCCGACnnnnnn 3' [SEQ ID NO: 4]
primer 2 (a pool of 4096 32-mers):
5 5' cgatagcagtagcatgcaggTCCGACnnnnnn 3' [SEQ ID NO: 5]

A nucleic acid preparation: is amplified, using primer 1 to randomly prime synthesis of sequences present therein. The starting nucleic acid molecules are cDNA or genomic DNA, either of which may comprise molecules that are substantially whole or that are into smaller pieces. Many DNA cleavage methods are well known in the art. Mechanical cleavage is achieved by several methods, including sonication, repeated passage through a hypodermic needle, boiling or repeated rounds of rapid freezing and thawing. Chemical cleavage is achieved by means which include, but are not limited to, acid or base hydrolysis, or cleavage by base-specific cleaving substances, such as are used in DNA sequencing (Maxam and Gilbert, 1977, *Proc. Natl. Acad. Sci. U.S.A.*, 74: 560–564). Alternatively, enzymatic cleavage that is site-specific, such as is mediated by restriction endonucleases, or more general, such as is mediated by exo- and endonucleases e.g. ExoIII, mung bean nuclease, DNAase I or, under specific buffer conditions, DNA polymerases (such as T4), which chew back or internally cleave DNA in a proofreading capacity, is performed. If the starting nucleic acid molecules (which may, additionally, comprise RNA) are fragmented rather than whole (whether closed circular or chromosomal), so as to have free ends to which a second sequence may be attached by means other than primed synthesis, the MmeI recognition sites may be linked to the starting molecules using DNA ligase, RNA ligase or terminal deoxynucleotide transferase. Reaction conditions for these enzymes are as recommended by the manufacturer (e.g. New England Biolabs; Beverly, Mass. or Boehringer Mannheim Biochemicals, Indianapolis, Ind.). If employed, PCR is performed using template DNA (at least 1 fg; more usefully, 1–1,000 ng) and at least 25 pmol of oligonucleotide primers; an upper limit on primer concentration is set by aggregation at about 10 μg/ml. A typical reaction mixture includes: 2 μl of DNA, 25 pmol of oligonucleotide primer, 2.5 μl of 10×PCR buffer 1 (Perkin-Elmer, Foster City, Calif.), 0.4 μl of 1.25 μM dNTP, 0.15 μl (or 2.5 units) of Taq DNA polymerase (Perkin Elmer, Foster City, Calif.) and deionized water to a total volume of 25 μl. Mineral oil is overlaid and the PCR is performed using a programmable thermal cycler. The length and temperature of each step of a PCR cycle, as well as the number of cycles, is adjusted in accordance to the stringency requirements in effect. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed below, 1–2 minutes), and extension (72° C. for 1 minute). Final extension is generally for 4 minutes at 72° C., and may be followed by an indefinite (0–24 hour) step at 4° C.

Annealing temperature and timing are determined both by the efficiency with which a primer is expected to anneal to a template and the degree of mismatch that is to be tolerated. In attempting to amplify a mixed population of molecules, the potential loss of molecules having target sequences with low melting temperatures under stringent (high-temperature) annealing conditions against the promiscuous annealing of primers to sequences other than their target sequence is weighed. The ability to judge the limits of tolerance for feature loss vs. the inclusion of artifactual amplification products is within the knowledge of one of skill in the art. An annealing temperature of between 30° C. and 65° C. is used. An example of one primer out of the pool of 4096 primer 1, one primer (primer 1 ex) is shown below, as is a DNA sequence from the preparation with which primer 1 ex has high 3' end complementarity at a random position. The priming site is underlined on either nucleic acid molecule.

primer 1 ex [SEQ ID NO: 7; bases 1–32]:
5'-gcagcagtacgactagcataTCCGACctgcgt-3'
genomic DNA [SEQ ID NO: 6]:
3'-tttcgacgcacatcgcgtgcatggccccatgcatcagg ctgacgaccgtcgtacgtctactcggct-5'

After priming, polymerase extension of primer 1 ex on the template results in:
[SEQ ID NO: 7]
5'-gcagcagtacgactagcataTCCGACctgcgtgtagcgcacgta ccggggtacgtagtcc gactgctggcagcatgcagatgagccga-3'

Out of the pool of 4096 primer 2, one primer with high 3' end complementarity to a random position in the extended primer 1 ex DNA is selected by a polymerase for priming (priming site in bold):
[SEQ ID NO: 7]
5'-gcagcagtacgactagcataTCCGACctgcgtgtagcgcacgt accggggtacgtagtcc gactgctggcagcatgcagatgagccga 3'
primer 2ex [SEQ ID NO: 8; bases 1–32]:
3'-gacgacCAGCCTggacgtacgatgacgatagc-5'

After priming and synthesis, the resulting second strand is:
[SEQ ID NO: 8]
3'-cgtcgtcatgctgatcgtatAGGCTGgacgcacatcgcgtgcatg gccccatgcatcagg ctgacgacCAGCCTggacgtacgatgacgatagc-5'

Primer 3, shown below, is a 26-mer that is identical to the constant region of primer 1 ex:
[SEQ ID NO: 7; nucleotides 1–26]
5'-gcagcagtacgactagcataTCCGAC-3'

It is immobilized by a 5' acrylyl group to a polyacrylamide layer on a glass slide.

Primer 4, below, is a 26-mer that is complementary to the constant region of primer 2ex:
[SEQ ID NO: 8; nucleotides 1–26]
5'-cgatagcagtagcatgcaggTCCGAC-3'

It is optionally immobilized to the polyacrylamide layer by a 5' acrylyl group.

The pool of amplified molecules derived from the sequential priming of the original nucleic acid preparation with mixed primers 1 and 2, including the product of 1 ex/2ex priming and extension, are hybridized to immobilized primers 3 and 4. In situ PCR is performed as described above, resulting in the production of a first random, immobilized array of nucleic acid molecules according to the invention. This array is replicated by the methods described in Example 1 in order to create a plurality of such arrays according to the invention.

After in situ PCR using primers 3 and 4:
5'-gcagcagtacgactagcataTCCGACctgcgtgtagcgcacgtacc ggggtacgtagt
3'-cgtcgtcatgctgatcgtatAGGCTGgacgcacatcgcgtgcatggc cccatgcatca ccgactgctgGTCGGAcctgcatgctactgctatcg-3' [SEQ ID NO: 9]

ggctgacgacCAGCCTggacgtacgatgacgatagc-5' [SEQ ID NO: 8]

After cutting with MmeI and removal of the non-immobilized strands:

[SEQ ID NO: 9; bases 1–46] 5'-gcagcagtacgactagcataTCCGACctgcgtgtagcgcacgt acc-3' (primer 1-based, clone-specific oligonucleotide)

[SEQ ID NO: 8; bases 1–46] 3'-ccatgcatcaggctgacgacCAGCCTggacgtacgatgacgat agc-5' (primer 2-based, clone-specific oligonucleotide)

The resulting random arrays of oligonucleotide primers representing the nucleic acid sequences of the original preparation are useful in several ways. Any particular feature, such as the above pair of primers, is used selectively to amplify the intervening sequence (in this case two central bp of the original 42 bp cloned segment are captured for each use of the chip or a replica) from a second nucleic acid sample. This is performed in solution or in situ, as described above, following feature identification on the array, using free, synthetic primers. If desired, allele-specific primer extension or subsequent hybridization is performed.

Importantly, this technique provides a means of obtaining corresponding, or homologous, nucleic acid arrays from a second cell line, tissue, organism or species according to the invention.

The ability to compare corresponding genetic sequences derived from different sources is useful in many experimental and clinical situations. By "corresponding genetic sequences", one means the nucleic acid content of different tissues of a single organism or tissue-culture cell lines. Such sequences are compared in order to study the cell-type specificity of gene regulation or MRNA processing or to observe chromosomal rearrangements that might arise in one tissue rather than another. Alternatively, the term refers to nucleic acid samples drawn from different individuals, in which case a given gene or its regulation is compared between or among samples. Such a comparison is of use in linkage studies designed to determine the genetic basis of disease, in forensic techniques and in population genetic studies. Lastly, it refers to the characterization and comparison of a particular nucleic acid sequence in a first organism and its homologues in one or more other organisms that are separated evolutionarily from it by varying lengths of time in order to highlight important (therefore, conserved) sequences, estimate the rate of evolution and/or establish phylogenetic relationships among species. The invention provides a method of generating a plurality of immobilized nucleic acid arrays, wherein each array of the plurality contains copies of nucleic acid molecules from a different tissue, individual organism or species of organism.

Alternatively, a first array of oligonucleotide primers with sequences unique to members of a given nucleic acid preparation is prepared by means other than the primed synthesis described above. To do this, a nucleic acid sample is obtained from a first tissue, cell line, individual or species and cloned into a plasmid or other replicable vector which comprises, on either side of the cloning site, a type IIS enzyme recognition site sufficiently close to the junction between vector and insert that cleavage with the type IIS enzyme(s) recognizing either site occurs within the insert sequences, at least 6 to 10, preferably 10 to 20, base pairs away from the junction site. It is contemplated that type IIS restriction endonuclease activity may even occur at a distance of up to pairs from the junction site. The nucleic acid molecules are cleaved from the vector using restriction enzymes that cut outside of both the primer and oligonucleotide sequences, and are then immobilized on a semi-solid support according to the invention by any of the methods described above in which covalent linkage of molecules to the support occurs at their 5' termini, but does not occur at internal bases. Cleavage with the type IIS enzyme (such as MmeI) to yield the immobilized, sequence-specific oligonucleotides is performed as described above in this Example.

As mentioned above, it is not necessary to immobilize primer 4 on the support. If primer 4 is left free, the in situ PCR products yield the upper (primer 1 derived) strand upon denaturation:

[SEQ ID NO: 9] 5'-gcagcagtacgactagcataTCCGACctgcgtgtagcgcacgt accggggtacgtagtcc gactgctgGTCGGAcctgcatgctactgctatcg-3'.

This sequence is available for hybridization to fluorescently-labeled DNA or RNA for mRNA quantitation or genotyping.

EXAMPLE 7

Isolation of a Feature from an Array of the Invention (Method 2)

As described above, laser-capture microdissection is performed in order to help orient a worker using the arrays of a set of arrays produced according to the invention, or to remove undesirable features from them. Alternatively, this procedure is employed to facilitate the cloning of selected features of the array that are of interest. The transfer of the nucleic acid molecules of a given feature or group of features from the array to a thin film of EVA or another heat-sensitive adhesive substance is performed as described above. Following those steps, the molecules are amplified and cloned as follows:

The transfer film and adherent cells are immediately resuspended in 40 $\mu$l of 10 mM Tris.HCl (pH 8.0), 1 mM EDTA and 1% Tween-20, and incubated overnight at 37° C. in a test tube, e.g. a polypropylene microcentrifuge tube. The mixture is then boiled for 10 minutes. The tubes are briefly spun (1000 rpm, 1 min.) to remove the film, and 0.5 $\mu$l of the supernatant is used for PCR. Typically, the sheets of transfer film initially applied to the array are small circular disks (diameter 0.5 cm). For more efficient elution of the after LCM transfer, the disk is placed into a well in a 96-well microliter plate containing 40 $\mu$l of extraction buffer. Oligonucleotide primers specific for the sequence of interest may be designed and prepared by any of the methods described above. PCR is then performed according to standard methods, as described in the above examples.

EXAMPLE 8

Excluded Volume Protecting Groups

The density of features of the arrays is limited in that they must be sufficiently separated to avoid contamination of adjacent features during repeated rounds of amplification and replication. This is achieved using dilute concentrations of nucleic acid pools, but results in density limited by the Poisson distribution to a maximum of 37% occupancy of available appropriately spaced sites. In order to increase the density of features while maintaining the spacing necessary to avoid cross contamination, the following approach may be taken.

An activity which can bind the nucleic acid molecules of the pool is positioned in spots on the surface of the array support to create a capture array. The spots of the capture array are arranged such that they are separated by a distance greater than the size of the spots (this is typically near the resolution of the intended detection and imaging devices, or approximately 3 microns). The size of the spots is set to be less than the diameter of the excluded volume of the nucleic acid polymer to be captured (for example, approximately one micron for 50 kb lambda DNA in 10 mM NaCl; please see Rybenkov et al., 1993, *Proc. Natl. Acad. Sci. U.S.A.* 90: 5307–5311, Zimmerman & Trach, 1991, *J. Mol. Biol.* 222: 599–620, and Sobel & Harpst, 1991, *Biopolymers* 31: 1559–1564, incorporated herein by reference, for methods of predicting excluded volumes of nucleic acids.

The "nucleic acid capture activity" of the array may be a hydrophilic compound, a compound which reacts covalently with the nucleic acid polymers of the pool, an oligonucleotide complementary to a sequence shared by all members of a pool (e.g., an oligonucleotide complementary to the 12 bp cohesive ends of a phage λ library, or oligonucleotide(s) complementary to one or both ends of a PCR-generated library containing large inserts and 6 to 50 bp of one strand exposed at one or both ends) or some other capture ligand including but not limited to proteins, peptides, intercalators, biotin, avidin, antibodies or fragments of antibodies or the like.

An ordered array of nucleic acid capture ligand spots may be made using a commercially-available micro-array synthesizer, modified inkjet printer (Castellino, 1997, supra), or the methods disclosed by Fodor et al. (U.S. Pat. No. 5,510,270), Lockhart et al. (U.S. Pat. No. 5,556,752) and Chetverin and Kramer (WO 93/17126). Alternatively, details on the design, construction and use of a micro-array synthesizer are available on the World Wide Web at www.cmgm.stanford.edu/pbrown.

An excess of nucleic acid or DNA is then applied to the surface of the microfabricated capture array. Each spot has multiple chances to bind a free nucleic acid molecule. However, once a spot has bound a nucleic acid molecule, it is protected from binding other molecules, i.e., the excluded volume of the bound DNA protects the spot from binding more than one molecule from the pool. Thus, saturation binding, or a situation very close to it, may be achieved while retaining the optimal spacing for subsequent amplification and replication.

The array resulting from this process may be amplified in situ and replicated according to methods described herein. Alternatively, or in addition, the array may be treated in a way which decreases the excluded volume of the captured group so that additional rounds of excluded volume protecting group (EVPG) addition may be performed. Arrays produced in this manner not only increase the efficiency of the array beyond that normally allowed by the Poisson distribution, but also can be of predetermined geometry and/or aligned with other microfabricated features. In addition, such arrays allow complicated highly parallel enzymatic or chemical syntheses to be performed on large DNA arrays.

EXAMPLE 9

Replica-destructive Amplification Methods

A major advantage of the replica amplification method is that because there are multiple copies of a particular array, information is not lost if a given replica is destroyed or rendered non-re-usable by a process. This allows the use of the most sensitive detection methods, regardless of their impact on the subsequent usefulness of that particular replica of the array. For example, tyramide-biotin/HRP (or other enzymatic in situ reactions) or biotin/avidin or antibody/hapten complexes (or other ligand sandwiches) may be used to effectively amplify the signal in a nucleic acid hybridization (or other bimolecular binding) experiment. These methods, however, may be considered destructive to the DNA array in that they involve interactions which are kinetically difficult to disrupt without destroying the array. Similarly, some detection processes, including sequencing by ligation and restriction and the variant methods described herein (see Examples 11 and 12), necessarily involve destruction, either chemically or enzymatically or both, of the template array. The availability of replica arrays made according to the methods disclosed herein allow the use of these methods, as they destroy only the replica, not the original or other copies.

The availability of replicas of an array allows the use of direct fluorescent detection of probes hybridized to the array without loss of the array for subsequent uses. One method which this allows is the relative quantitation of mRNA by hybridization of the array with fluorescently labeled total cDNA probes. This method allows the evaluation of changes in the expression of a wide array of genes in populations of RNA isolated from cells or tissues in different growth states or following treatment with various stimuli.

Fluorescently labeled cDNA probes are prepared according to the methods described by DeRisi et al., 1997, *Science* 278: 680–686 and by Lockhart et al., 1996, *Nature Biotechnol.* 14: 1675–1680. Briefly, each total RNA (or mRNA) population is reverse transcribed from an oligo-dT primer in the presence of a nucleoside triphosphate labeled with a spectrally distinguishable fluorescent moiety. For example, one population is reverse transcribed in the presence of Cy3-dUTP (green fluorescence signal), and another reverse transcribed in the presence of Cy5-dUTP (red fluorescence signal).

Hybridization conditions are as described by DeRisi et al. (1997, supra) and Lockhart et al. (1996, supra). Briefly, final probe volume should be 10–12 μl, at 4×SSC, and contain non-specific competitors (e.g., poly dA, $C_0T1$ DNA for a human cDNA array) as required. To this mixture is added 0.2 μl of 10% SDS and the probes are boiled for two minutes and quick chilled for ten seconds. The denatured probes are pipetted onto the array and covered with a 22 mm×22 mm cover slip. The slide bearing the array is placed in a humid hybridization chamber which is then immersed in a water bath (62° C.) and incubated for 2–24 hours. Following incubation, slides are washed in solution containing 0.2× SSC, 0.1% SDS and then in 0.2×SSC without SDS. After washing, excess liquid is removed by centrifugation in a slide rack on microtiter plate carriers. The hybridized arrays are then immediately ready for scanning with a fluorescent scanning confocal microscope. Such microscopes are commercially available; details concerning design and construction of a scanner are also available on the World Wide Web at www.cmgm.stanford.edu/pbrown.

In the above example in which one population of RNA was reverse-transcription labeled with Cy3 and the other with Cy5 fluorescent dyes, the relative expression of genes represented by the features of the micro-array may be evaluated by the presence of green (Cy3, indicating the mRNA from this population hybridizes to a given feature), red (Cy5, indicating the mRNA from this population hybridizes to a given feature) or yellow (indicating that both MRNA populations used to make probes contain mRNAs which hybridize to a given feature) fluorescent signals.

Alternatively, separate replicas of the same array may be hybridized separately with probes labeled with the same fluorescent dye marker but made from different populations of mRNA. For example, cDNA probes made from cells before and after treatment with a growth factor may be hybridized with separate replicas of a genomic array made from those cells. The intensity of the signal of each feature may be compared before and after growth factor treatment to yield a representation of genes induced, repressed, or whose expression is unaffected by the growth factor treatment. This method requires that the replica arrays contain one or more markers which will not vary as a means of aligning the hybridized arrays. Such a marker may be a foreign or synthetic DNA, for example. The RNA corresponding to such a marker is spiked at equal concentration into the reverse transcription reactions used to generate labeled cDNA probes. Prior to the first hybridization with experimental cDNAs, a control hybridization using only the marker cDNA may be performed on a replica array to precisely determine the position(s) of the marker(s) within the array.

In either the simultaneous hybridization or the separate hybridization methods, the availability of additional replicas of the array allows further characterization (including but not limited to sequencing and isolation of the gene represented by the feature) of those features of the array which exhibit particular expression patterns.

EXAMPLE 10

Geometrical Focusing

A characteristic of the replica amplification process is that each replica will tend to occupy a larger area than the feature from which it was made. This is because the feature molecules transferred to the replica may come from anywhere within the circumferential area occupied by the template feature. Subsequent amplification of the transferred molecules will necessarily increase the area occupied by the feature relative to that occupied by the template feature. It is clear that this phenomenon will limit the practical number of times an array may be sequentially replicated without contamination of surrounding features. There are several approaches to solving this problem.

First, as mentioned previously, more than one replica of an amplified array may be made per amplification. It is clear that the "earlier" in the replication process a given array is replicated, the less area its features will occupy relative to those made later. That is, the more replicas one can make of an original amplified array before re-amplifying the template, the more arrays with smaller features one will have. The number of replicas of a given array which may be made without re-amplification of the template may be determined empirically by, for example, hybridization of a sequential series of amplified replicas from a single array with an oligonucleotide which hybridizes with a sequence common to every feature. Comparison of the hybridization signals from the first replica to those of subsequent replicas made from the same template without re-amplification of the template will indicate at what point features begin to be lost from the replicas.

Second, one may reduce the number of PCR cycles used in the amplification process. Because the amplification is exponential, a small change in the cycle number can have a profound influence on the area occupied by the feature. This will clearly not solve the problem completely, but when combined with the first approach it can extend the useful number of cycles of amplification and replication for a given array. The practical number of PCR cycles to use for each round of amplification may also be estimated empirically by making several replicas from a single template array without re-amplification, and then subjecting individual replicas in the series to increasing numbers of PCR cycles. For example, replicas may be subjected to 10, 20, and 30 amplification cycles, followed by hybridization with a fluorescent probe sequence common to all features of the array. Visualization of the hybridized array by fluorescence microscopy will indicate at which point the features begin to intrude upon one another. Clearly, the starting size of the feature will influence the number of PCR cycles allowable per replication cycle, but it is within the ability of one skilled in the art to determine generally how many cycles are optimal to obtain enough DNA for subsequent rounds of replica amplification without widespread contamination of surrounding features.

A third approach recognizes the fact that the amplified features occupy more than just the two dimensional area of the surface they sit upon. Rather, each amplified feature occupies a hemishperical space with a radius, r. If the features are situated on one slide, which for discussion will be designated the "bottom" slide, and covered by another slide (the "top" slide) set at a uniform, fixed distance from the bottom slide, one will note that as the hemishperical feature expands with rounds of amplification, the portion of the growing hemisphere which first contacts the top slide will be much smaller in cross-sectional area than the portion in contact with the bottom slide. This presents a smaller surface area, with all sequence information intact, from which to make replicas that do not occupy greater surface area than their template features. This method will be referred to as "geometrical focusing."

For example, after 30 cycles in 15% polyacrylamide, 500 bp amplicons will form hemispheres with a 10 micron radius. The length of the template and the percentage of acrylamide in the gel influence the size of the amplified features such that, for a given number of cycles, the size of the features decreases as the length of the template or the percentage of acrylamide increases. In general, the size of an amplified feature with respect to a given number of amplification cycles under given conditions is determined empirically by visualizing it with a fluorescent confocal microscope or fluorimager after staining with a fluorescent intercalator. Labeled primers or nucleotides may also be used to "light up" the feature for measurement by this method.

The distance between the surface bearing the array and the surface the array is to be transferred to may be controlled using plastic spacers of the desired thickness along the edges of the slide. A small volume of polyacrylamide solution plus capillary action will take the volume out to the edges of a predetermined area of coverslip.

Another contemplated method of regulating or controlling the distance between surfaces in the geometrical focusing method involves the use of optical feedback, such as Newton rings or other interferometry, to adjust pressure locally across the surfaces. The adjustment may be accomplished by a scanning laser that heats a differential thermal expansion plate differentially based on the optical feedback.

As mentioned above, bioactive substances such as enzymes may be cast directly in polyacrylamide gels. Other reagents, including buffers and oligonucleotide primers may be either cast into the gels or added by diffusion or even electrophoretic pulses to the pre-formed gel matrices. If the upper plate has little or no adhesiveness to the gel (achieved, for example, through silane coating as described above), then when it is removed, the upper circle of each hemisphere is the only exposed DNA. Some of the exposed DNA can be transferred by microcontact printing using either plate, or by another round of polymerization from the upper plate. The radius of the circle exposed for transfer will be $c=\sqrt{r^2-d^2}$, where r is the radius of the hemisphere and d is the distance between the plates. Therefore, when r=10 microns and d=8 microns, the radius of the exposed circle, c=6 microns, less than the size of the template feature. This exposed circle will thus have a cross-sectional area less than that occupied by the template feature, referred to as q, at the surface of the support. This slight reduction in the radius, and consequently the cross-sectional area of the transferred feature will work to keep the amplified replica features sharper through several rounds of replication. The distance between the plates may be 10%, 20%, 30%, 40%, on up to 50% or more less than the radius of the features being transferred. The surface area (of the support) occupied by the transferred features may be considered reduced or lessened if it is 10%, 20%, 30%, 40%, on up to approximately 80% less than the area occupied by features on the template array. The resolution of the features is considered to be preserved if the features remain essentially distinct after amplification of the transferred nucleic acid. It is noted that features which amplify with lower efficiency than others may be lost if the distance between plates is too large. Therefore, geometrical focusing will be most useful when combined with the other two approaches described for limiting the size of amplified replicas. That is, the number of replicas made from individual arrays early in the process should be maximized while the number of PCR cycles per amplification should be minimized.

EXAMPLE 11

Replica Sequencing with Ligation/restriction Cycles

The sequencing by ligation and restriction method of Brenner, as described above, provides a powerful approach to the simultaneous sequencing of entire arrays of DNA molecules. The ability to replicate the entire array provides a novel approach to improving the efficiency of the sequencing method. In its standard format, the number of bases sequenced by the ligation and restriction method is limited by a background of molecules which fail to ligate or cleave properly in a given cycle. This phenomenon disturbs the synchrony of the process and limits the effective lengths which may be sequenced by this method since the interference it introduces is cumulative.

The sequencing by ligation and restriction method as disclosed by Brenner addresses this issue by the optional inclusion of a "capping" step after the unligated probe has been removed. According to that method, when the target molecules have a 5' protruding end, a mixture of dideoxynucleoside triphosphates and a DNA polymerase is added prior to the next cleavage step. This results in the addition of a single dideoxynucleotide to the 3' terminus of the recessed strand which will prevent subsequent ligation steps, effectively deleting the molecule which failed to be ligated from the target population. The effectiveness of the capping method is dependent on the completeness of the cap addition.

An improvement on the method of sequencing by ligation and cleavage involves the use of two or more distinct probes comprising different "ligation cassettes" coupled with a round of replica amplification by PCR wherein one of the primers is specific to the most recently added ligation cassette. This method will be referred to as "replica sequencing with ligation and restriction cycles." A probe of use in this method is a double-stranded polynucleotide which (i) contains a recognition site for a nuclease, (ii) typically has a protruding strand capable of forming a duplex with a complementary protruding strand of the target polynucleotide, and (iii) which has a sequence, the "ligation cassette," such that an oligonucleotide primer complementary to one such sequence or cassette will allow amplification of the molecule to which it is ligated under the conditions used for annealing and extension within the method.

In each sequencing cycle, only those probes whose protruding strands form perfectly-matched duplexes with the protruding strand of the target polynucleotide hybridize and are then ligated to the end of the target polynucleotide. The probe molecules are divided into four populations, wherein each such population comprises one of the four possible nucleotides at the position to be determined, each labeled with a distinct fluorescent dye. The remaining positions of the duplex-forming region are occupied with randomized, unlabeled bases, so that every possible multimer the length of that region is represented; therefore, a certain percentage of probe molecules in each pool are complementary to the single-stranded region of the target polynucleotide; however, only one pool bears labeled probe molecules that will hybridize.

The individual probes comprising different ligation cassettes may have a recognition sequence for the same or different type IIs restriction endonuclease. The important factor is that the ligation cassette sequences, due to their distinct primer binding characteristics, allow amplification of only those target molecules which were successfully ligated in the previous ligation step. This also enforces the requirement for completing the cleavage step, as those target molecules which were not cleaved in the previous step will similarly not be amplified, since they will not bear the proper primer. This process enriches the proportion of each feature which has successfully completed the most recent cycle of ligation and restriction. Through the reduction in background due to improved synchrony, this method increases the number of bases which can be sequenced for features on a given array. The added steps of the replication and subsequent re-amplification of the array not only further enrich for sequences which are in synchrony, but also confers control over the size of the features, as described herein in the section entitled "Geometrical Focusing". As discussed in that section, control over the size of the features with increasing numbers of amplification or replication cycles allows more sequence or other information to be gleaned from a given array before features begin to overlap.

After a cycle of cleavage, ligation of a first ligation cassette, and subsequent detection of the next base in the sequence, the steps one will perform in applying the replica amplification process to this method of sequencing are as follows: 1) using primers, one complementary to the common end (arbitrarily designated the 5' end, for this discussion) of the features being sequenced, and the other complementary to the most recently added ligation cassette, the features of the array are amplified and then replicated according to methods described herein above; 2) a replica is then subjected to a new cycle of cleavage, ligation of a probe comprising a distinct ligation cassette, and detection of the next base in the sequence; 3) the features of the array are amplified using the primer complementary to the common 5' end of the features and a primer complementary to the distinct ligation cassette, followed by replication of the array; and 4) the process of steps 1–3 is repeated until the sequences of the features are determined.

Within the method of replica sequencing with ligation and restriction cycles, a new probe comprising a distinct ligation cassette sequence may be used for each cycle of ligation and restriction. Alternatively, fewer different ligation cassettes than the number of cycles of ligation and restriction may be used. In other words, as few as two and as many as n (where n equals the number of cycles of ligation and restriction) different ligation cassettes may be of use according to the method. As used herein, "new" or "different" or "distinct" when referring to probes or ligation cassettes comprised by probes is meant to indicate that the sequence of each ligation cassette, or the oligonucleotide probe comprising it, is such that a primer complementary to the ligation cassette will not hybridize with any other cassette or oligonucleotide comprising a cassette under the conditions used for annealing and polymerization. Clearly, the greater the number of different ligation cassettes used, the more strictly the requirement for completion of previous cycles will be enforced. It is within the ability of one of skill in the art to determine how many different ligation cassettes are required to achieve a desired level of synchrony (with a concomitant reduction in background). As a general guideline, since the background due to incomplete cycles is cumulative, the number of ligation cassettes will vary in proportion to the desired number of bases to be sequenced. One would, for example, expect to use a larger number of different ligation cassettes if 300 bases are to be sequenced than one would use to sequence 30 bases.

Replication of the arrays in the method of replica sequencing by ligation and restriction may be performed as often as every cycle, once every nth cycle (where n is greater than 1), or even once per whole set of cycles. Again, the frequency of replication may be determined by one skilled in the art. Considerations include, but are not limited to the physical size of the features and the overall desired number of bases to be sequenced.

The method of Jones, 1997, *Biotechniques* 22: 938–946 teaches the use of PCR amplification to positively select for those molecules in a population which had successfully completed the previous cycle of cleavage and ligation. Jones did not, however, teach the replication of amplified populations or the application of the method to random arrays of features. Rather, Jones taught the use of microwell plates and a robotic pipetting apparatus to perform his method. An important advantage of the incorporation of the replication step into the sequencing method is that it allows control over the size of the amplified features. While Jones mentions the eventual application of his method to the "biochip" format, no guidance is given which would allow one to overcome the inherent limitation on the size of the features in a method incorporating PCR amplification steps on a microarray. In contrast, novel methods based on the replication of arrays, such as geometrical focusing, are described herein which overcome this limitation.

EXAMPLE 12

Non-replica Sequencing

Methods allowing determination of DNA sequences on an array that do not involve replica production are also preferred for some applications. For example, sequencing of transcription products (or their reverse transcripts) in situ requires that the fine resolution of the sequencing templates be preserved.

One may use the method of Jones (1997, supra) to sequence features on an array without replicating the array. Other non-electrophoretic methods which might be adapted to sequencing of microarrays include the single nucleotide addition methods of minisequencing (Canard & Sarfati, 1994, *Gene* 148: 1–6; Shoemaker et al., 1996, *Nature Genet.* 14: 450–456; Pastinen et al., 1997, *Genome Res.* 7: 606–614; Tully et al., 1996, *Genomics* 34: 107–113; Jalanko et al., 1992, *Clin. Chem.* 38: 39–43; Paunio et al., 1996, *Clin Chem.* 42: 1382–1390; Metzker et al., 1994, *Nucl. Acids. Res.* 22: 4259–4267) and pyrosequencing (Uhlen & Lundeberg, U.S. Pat. No. 5,534,424; Ronaghi et al., 1998, *Science* 281: 363–365; Ronaghi et al., 1999, *Anal Biochem.* 267: 65–71).

As an alternative to minisequencing or pyrosequencing, the novel method of fluorescent in situ sequencing extension quantification (FISSEQ) may be used. FISSEQ involves the following steps: 1) a mixture of primer, buffer and polymerase are added to a microarray of single stranded DNA; 2) a single, fluorescently labeled base is added to the mixture, and will be incorporated if it is complementary to the corresponding base on the template strand; 3) unincorporated dNTP is washed away; 4) incorporated dNTP is detected by monitoring fluorescence; 5) steps 2–4 are repeated (using fresh buffer and polymerase) with each of the four dNTPs in turn; and 6) steps 2–5 are repeated in cycles until the sequence is known.

It is recognized that polymerases used for sequencing become inefficient for further extension when 100% of bases added to a primer are non-native (i.e., fluorescently labeled). Therefore, the efficiency of FISSEQ may be further improved by employing a mixture of native and fluorescently labeled dNTP. The mixture allows incorporation of labeled bases at each position without requiring 100% adjacent non-native bases. Also, a photobleaching step after each set of one or more cycles may be incorporated to allow the background subtraction to act on a smaller number, with corresponding lower Poisson shot noise.

As an alternative to photobleaching or computational subtraction of accumulating fluorescence, it is contemplated that cleavable linkages between the fluorophore and the nucleotide may be employed. Cleavage may be accomplished, for example, by acid or base treatment, or by oxidation or reduction of the linkage. For example, a disulfide linkage may be reduced using thiol compounds such as dithiothreitol. Similarly, a cis-glycol linkage can be cleaved by periodate. These are examples of standard components of cleavable cross-linkers used for protein chemistry or for polyacrylamide gels. In this embodiment, cleavage could be done as often as every cycle, or less frequently, such as every other, every third, or every fifth or more cycles.

A modified embodiment of FISSEQ that allows longer effective reads involves extension for a fixed number of cycles with mixtures of three native (unlabeled) dNTPs interspersed with pulses of wash, up to a desired length. Following this, one begins cycles of adding one partially labeled (i.e., mixture of labeled and unlabeled) dNTP at a time. The triple dNTP cycles allow positioning of the polymerase a fixed distance from the primer and would use alternating sets of triphosphates (e.g., ACG, CGT, ACG, . . . ) chosen and concentration optimized to reduce false incorporation and failure to incorporate (Hillebrand et al., 1984, *Nucl. Acids. Res.* 12: 3155–3171). This allows three times longer reads plus any advantage possibly conferred by having fewer potential misincorporation steps. It is contemplated that if the misincorporation rate (n-1 and extensible n+1 products) can be as low as $10^{-4}$, then read lengths longer than current electrophoresis-based methods are possible.

Another modification using the triple dNTP cycles is aimed at reducing the background caused by mismatch incorporation. If, for example, G:T mismatch pairing is a major source of misincorporation (Keohavong et al., 1993, *PCR Meth. Appl.* 2: 288–292), one should always include A with G, since the more stable A:T interaction will be favored over the less stable G:T interaction. For example, one may alternate triple mix 1 (dATP, dCTP, dGTP) with triple mix 2 (dCTP, dGTP, dTTP).

A more conservative version of FISSEQ which can allow determination of longer stretches of sequences at a time requires replicas of the array, and will be referred to as replica-FISSEQ. Replica arrays for this method may be made by the replica amplification methods described herein, or by a microarray spotting method using a microarray robot. By spotting the same DNA templates in known positions on the slide, the same effect can be obtained as with the replica-amplified features. In this embodiment, 30 identical arrays are made using the microarray robot. Stepping through 1 to 30 additions with native (unlabeled) dNTPs sets up the final base to be assessed for each array element. The final base is assessed by the sequential addition of each fluorescent dNTP as is normally done in minisequencing. Pyrosequencing data (Ronaghi et al., 1998, *Science* 281: 363) has shown that the polymerase extension reactions stay accurately in phase through at least 30 cycles of dNTP addition using natural nucleotides and Klenow exo- polymerase. To read out N bases with the single slide method described above requires 4N cycles of nucleotide addition and washing. The N-slide (triple dNTP, 4 cycles per slide) method (using N replicas), requires 2N(N−1)/3 cycles. The actual read lengths will be more than N bases (1.4N on average due to runs of identical bases). The same number of scans are required for the two methods.

Several other modifications to the basic method of FISSEQ are contemplated. For example, a loop may be incorporated into the primer to help reduce mispriming events (Ronaghi et al., 1998, *Biotechniques* 25: 876–878, 880–882, and 884). A particularly useful loop structure, described by Hirao et al. (1994, *Nucl. Acids Res.* 22: 576–582) as "extraordinarily stable," would have the advantage of having a relatively short stem, lowering the stability of the complementary strand hairpin, the result being that the asymmetric PCR for the strand that we want will extend to the correct end more efficiently.

Another modification would address the difficulty, encountered in many methods, of sequencing past long repeating stretches. If it is known that a given array contains many such sequences, one may include a defined regimen (for example, halfway through the whole sequence) of deoxy- and dideoxynucleotides to reduce out-of-phase templates. That is, if one knows he or she is sequencing through a repeat of, for example, AC dinucleotides, one may reduce the number of out-of-phase molecules by following a dATP addition with a ddATP addition. Only those molecules which failed to incorporate the deoxy- form of the nucleotide will be available to incorporate the dideoxy- form, leading to chain termination and reduction of that source of background. Clearly, similar regimens may be devised for repeats involving more than two nucleotides. It should be noted that the strategy is not limited to repeats and may be used to extend read length in any situation where most of the sequences in the array have a block of sequence part of the way through the target sequence which is known. For example, in an array of targets, most having the unique sequence ACGTA at the same distance from the primer, one may reduce the number of out-of-phase molecules by following a dATP addition with a ddATP, ddGTP, and ddTTP addition, then dCTP followed by ddATP, ddCTP, and ddTTP addition.

EXAMPLE 13

Gel Sequencing of Amplified Array Features using Dye Terminators

In addition to the methods of sequencing by hybridization and sequencing by ligation and restriction, it is possible to sequence amplified features of arrays using fluorescently labeled dideoxynucleoside triphosphates ("dye terminators") using the Sanger ("dideoxy") sequencing method (Sanger et al., 1975, *J. Mol. Biol.*, 94:441) and a micro gel system. In this embodiment, the array of amplified features is created in a linear arrangement along one edge of a very thin slab gel or at the edge of a microfabricated array of capillaries. DNA molecules of the pool to be sequenced are prepared in any of the same ways as for the random array spot format described above, such that each molecule in the pool has a known sequence or sequences at one or both ends which may serve as primer binding sites. The DNA is applied to the slide as in the random array format, except that it is restricted to a thin line, rather than a circular spot.

Alternatively, the DNA may be derived as a replica of a line within a standard 2D array, or may be derived as a replica of a line from a metaphase chromosome spread.

Features of the deposited linear array are then amplified using any of the methods described above for amplification of spot arrays. This amplification may be linear or exponential, thermocycled or isothermal. Isothermal amplification methods include the Phi29 rolling circle amplification method (Lizardi et al., 1998, *Nature Genetics* 19: 225–232), reverse transcriptase/T4 DNA polymerase/ Klenow/T7 RNA polymerase linear amplification (Phillips and Eberwine, 1996, *Methods* 10: 283–288) and a T7 DNA polymerase/thioredoxin/ssb system (Tabor and Richardson, January 1999 *Department of Energy Human Genome Program Abstract* No. 15).

The amplified DNA template may be replicated using the methods described above. This template, which is immobilized either covalently, by entanglement, or by steric hindrance of the gel (or other semi-solid) is then reacted with dye terminators in the presence of the other necessary components of the dideoxy sequencing method (i.e., primer, dNTPs, buffer and polymerase). It is well known in the art that a number of polymerases may be used for dideoxy- sequencing, including but not limited to Klenow polymerase, Sequenase™ or Taq polymerase. A major advantage of dye terminators over fluorescently labeled primers ("dye primers") is that the use of dye terminators requires only one reaction containing four distinguishably labeled terminators, whereas the use of dye primers requires four separate reactions which would require four identical amplified features and software alignment of the post-size- separation pattern. It should be noted that dye terminators also exist for RNA polymerase sequencing (Sasaki et al., 1998, *Proc. Natl. Acad. Sci. U.S.A.* 95: 3455–3460). It should also be noted that if the termination reactions have been performed with the use of primers, then a rare-cutting endonuclease may be used to produce a desired end for the sequencing ladder.

A miniature gel system appropriate for the gel sequencing of linear feature arrays has been described by Stein et al., 1998, *Nucl. Acids. Res.* 26: 452–455. In this system, small, ultrathin polyacrylamide gels are cast, eight or more at a time, on standard microscope slides. The gels may be stored, ready to use, for approximately two weeks. They are run horizontally in a standard mini-agarose gel apparatus, with typical run times of 6 to 8 minutes. Stein et al. describe a novel sample loading system which permits volumes as low as 0.1 µl to be analyzed. The band resolution compares favorably with that of large-format sequencing gels. Within the context of the sequencing of linear arrays according to the invention, the sample loading is accomplished by performing the termination reactions within, or at the very edge of the gel, rather than by mechanical means.

Since the terminated reaction products remain bound to the template, the reaction may be cleaned of dNTPs, primers and salts by diffusion, flow and/or electrophoresis. The termination products are then denatured and electrophoresed perpendicular to the line of amplified features in a thin slab or capillary format. An important aspect of this method is that the order of the amplified features is preserved throughout the process. Thus, if the line of features comes from a chromosome or large cloned or uncloned DNA fragment, the long range order is preserved and greatly aids in the assembly of complex genomic regions even in the presence of long repeats. Similarly, if the lines of features are derived as replicas of lines from the standard 2D arrays, the sequence identity of each spot in that line may be determined. Similar replicas of additional lines from the 2D spot may be used to determine the identity of each spot or feature of the 2D array. In addition to the clear advantages regarding the spatial organization of the features, this method has the additional advantage of actually using more of the sequencing reaction than other methods. That is, all of the reaction products are electrophoresed, rather than just a portion of it, meaning there is less waste of reagents. Further, the immobilization of the features allows the use of a common pool of reagents to sequence many features simultaneously. Thus, the method is more economical on a per sequence basis.

EXAMPLE 14

Multiplex PCR

Multiplex PCR refers to the process of amplifying a number of different DNA molecules in the same PCR reaction. Generally the process involves the addition of multiple primer pairs, each pair specific for the amplification of a single DNA target species. A major goal of investigators is to apply the power of multiplex PCR to the problem of high throughput genotyping of individuals for specific genetic markers. If 100,000 polymorphic markers are to be assayed per genome, it would be very expensive to perform 100,000 individual PCR reactions. Some advances have been made in multiplexing PCR reactions (Chamberlain et al., 1988, *Nucl. Acids Res.* 16:11141), and the degree of multiplexing of the PCR has been scaled up, followed by hybridization to an array of allele-specific probes (Wang et al., 1998, *Science* 280: 1077). However, in the studies by Wang et al., the percentage of PCR products that successfully amplified decreased as the number of PCR primers added to the reaction increased. When approximately 100 primer pairs were used, about 90% of the PCR products were successfully amplified. When the number of primer pairs was increased to about 500, about 50% of the PCR products were successfully amplified.

The decreasing efficiency with increasing number of primers is due in large part to the phenomenon of "primer dimer" formation. Primer dimers are the result of fortuitous 3' terminal complementarity of 4 bp or more between primers. This complementarity allows hybridization which is stabilized by polymerase recognition and extension of both strands. After the first cycle of extension, the complementarity is no longer limited to the 3' terminal nucleotides; rather, the entire primer dimer is now complementary to the primers. This reaction efficiently competes with the desired amplification reaction, in part because the concentration of the primers is significantly greater than that of the desired amplification target, kinetically favoring the amplification of the primer dimers. This phenomenon increases with increasing numbers and concentrations of primers.

A new approach to solving these inherent problems with multiplex PCR uses microarrays of immobilized, amplified PCR primers. By immobilizing at least one of the PCR primers, the method reduces the possibilities for non-specific primer interactions. The local concentration of primers is high enough for amplification, yet the individual primers are restricted from interacting non-specifically with one another.

Another disadvantage of standard multiplex PCR is that individual primer pairs must be synthesized for each polymorphic target. Genotyping DNA with 100,000 polymorphism targets would require, in theory, 200,000 different PCR primers. Not only is the synthesis of such primers costly and time consuming, but not all primer designs succeed in producing a desired PCR product. Therefore considerable time and energy will be spent optimizing the primer designs.

According to the new multiplex PCR method, one of the primers has a 5' end which is generic for the entire multiplex PCR reaction, such that the entire multiplex reaction will have that segment on the "mobile" primer. This 5' generic sequence may contain a restriction site for later cloning, a bacteriophage or other promoter for transcription of the products, or some other useful or identifiable sequence. The 3' end of the mobile primer is complementary to any genomic (or cDNA) sequence which is to be amplified at a reasonable PCR distance from the 3' end of the immobile primer. In other words, the 3' end of the mobile primer is randomized. The length of the randomized 3' sequence may be as few as 5 nucleotides, up to 10 nucleotides or more. The second, or "specific" primers are immobilized (according to methods known in the art or described herein) to keep them from diffusing into the other primer pair zones while the mobile primer allows the extended product to diffuse.

There are at least two ways primer pairs may be distributed. First, two presynthesized Acrydite primers may be codeposited (Kenney et al., 1998, *Biotechniques* 25: 516–521; Rehman et al., 1999, *Nucl. Acids. Res.* 27: 649–655), along with template and polymerase, in a gel volume element, for example by aerosol, emulsion, or inkjet printer, from an equimolar primer mixture. Alternatively, the primers may be derived from genomic DNA by a localized PCR. Generic primers can be used with one immobilized primer to make amplified features, and then release the new extended primers by exonuclease or type II restriction enzymes as described elsewhere herein. The new extended primers would then be copolymerized, along with template and polymerase, into the gel.

The process of this modified multiplex PCR method can be thought of as essentially two different steps. In the first, primers immobilized in a microarray hybridize with their complementary sequence in the template and are extended. In the second, and subsequent steps, the 3' (randomized) end of the mobile primers hybridizes at some point along the length of the extended immobilized primer and is itself extended. In subsequent cycles, other molecules in the immobilized primer features hybridize with the products of the previous extension, allowing extension, and so on, yielding exponential amplification as in standard PCR.

The multiplex PCR strategy need not involve replica printing.

USE

The invention is useful for generating sets each comprising a plurality of copies of a randomly-patterned, immobilized (thus highly reusable) nucleic acid arrays from a first array upon which the molecules of a nucleic acid pool are randomly positioned quickly, inexpensively and from unique pools of nucleic acid molecules, such as biological samples. The sets of arrays, and members of such sets, produced according to the invention are useful in expression analysis (Schena, et al., 1996, Proc. Nat. Acad. Sci. U.S.A., 93: 10614–10619; Lockhart, et al., 1996, Nature Biotechnology, 14: 1675–1680) and genetic polymorphism detection (Chee et al., 1996, Science, 274(5287): 610–614). They are also of use in DNA/protein binding assays and more general protein array binding assays. The methods of the invention are also useful for determining the sequences of nucleic acids on arrays.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method of amplifying a plurality of nucleic acids, said method comprising the steps of:
   a) creating an array of immobilized oligonucleotide primers, wherein the primers are immobilized on a semi-solid support;
   b) hybridizing amplification template to immobilized oligonucleotide primers,
   c) extending the immobilized oligonucleotide primers using a DNA polymerase activity, and deoxynucleotide triphosphates to form immobilized nucleic acid strands and then denaturing the amplification template from the immobilized nucleic acid strands;
   d) hybridizing non-immobilized oligonucleotide primers to the immobilized nucleic acid strands and extending :the non-immobilized oligonucleotide primers and denaturing the extended nonimmobilized oligonucleotide primers from the immobilized nucleic acid strands, and
   e) repeating steps (b) and (c) and (d) for a defined number of cycles to yield a plurality of amplified nucleic acid molecules.

2. A method of amplifying a plurality of nucleic acids, said method comprising the steps of:
   a) creating an array of immobilized oligonucleotide primers,
   b) hybridizing amplification template to immobilized oligonucleotide primers,
   c) extending the immobilized oligonucleotide primers using a DNA polymerase activity, and deoxynucleotide triphosphates to form immobilized nucleic acid strands and then denaturing the amplification template from the immobilized nucleic acid strands;
   d) hybridizing non-immobilized oligonucleotide primers to the immobilized nucleic acid strands and extending the non-immobilized oligonucleotide primers and denaturing the extended nonimmobilized oligonucleotide primers from the immobilized nucleic acid strands, and
   e) repeating steps (b) and (c) and (d) for a defined number of cycles to yield a plurality of amplified nucleic acid molecules, wherein said non-immobilized oligonucleotide primer comprises a pool of oligonucleotide primers comprised of 5' and 3' sequence elements, said 5' sequence element identical in all members of said pool, and said 3' sequence element containing random sequences.

3. The method of claim 2 wherein said 5' sequence element comprises a restriction endonuclease recognition sequence.

4. The method of either of claims 2 or 3 wherein said 5' element comprises a transcriptional promoter sequence.

5. A method of amplifying a plurality of nucleic acids, said method comprising the steps of:
   a) creating an array of immobilized oligonucleotide primers,
   b) hybridizing amplification template to immobilized oligonucleotide primers,
   c) extending the immobilized oligonucleotide primers using a DNA polymerase activity, and deoxynucleotide triphosphates to form immobilized nucleic acid strands and then denaturing the amplification template from the immobilized nucleic acid strands;
   d) hybridizing non-immobilized oligonucleotide primers to the immobilized nucleic acid strands and extending the non-immobilized oligonucleotide primers and denaturing the extended nonimmobilized oligonucleotide primers from the immobilized nucleic acid strands, and
   e) repeating steps (b) and (c) and (d) for a defined number of cycles to yield a plurality of amplified nucleic acid molecules, wherein said immobilized oligonucleotide primers of said array of step (a) are heterogenous in nucleic acid sequence.

6. A method of amplifying a plurality of nucleic acids, said method comprising the steps of:
   a) creating an array of immobilized oligonucleotide primers,
   b) hybridizing amplification template to immobilized oligonucleotide primers,
   c) extending the immobilized oligonucleotide primers using a DNA polymerase activity, and deoxynucleotide triphosphates to form immobilized nucleic acid strands and then denaturing the amplification template from the immobilized nucleic acid strands;
   d) hybridizing non-immobilized oligonucleotide primers to the immobilized nucleic acid strands and extending the non-immobilized oligonucleotide primers and denaturing the extended nonimmobilized oligonucleotide primers from the immobilized nucleic acid strands, and
   e) repeating steps (b) and (c) and (d) for a defined number of cycles to yield a plurality of amplified nucleic acid molecules, wherein said immobilized oligonucleotide primers are generated from genomic DNA.

7. A method of amplifying a plurality of nucleic acids, said method comprising the steps of:
   a) creating an array of immobilized oligonucleotide primers,
   b) hybridizing amplification template to immobilized oligonucleotide primers,
   c) extending the immobilized oligonucleotide primers using a DNA polymerase activity, and deoxynucleotide triphosphates to form immobilized nucleic acid strands and then denaturing the amplification template from the immobilized nucleic acid strands;
   d) hybridizing non-immobilized oligonucleotide primers to the immobilized nucleic acid strands and extending the non-immobilized oligonucleotide primers and denaturing the extended nonimmobilized oligonucleotide primers from the immobilized nucleic acid strands, and
   e) repeating steps (b) and (c) and (d) for a defined number of cycles to yield a plurality of amplified nucleic acid molecules, wherein the array, template, non-immobilized primer, and polymerase are cast in a polyacrylamide gel.

8. The method of claim 4 wherein the array, template, non-immobilized primer, and polymerase are cast in a polyacrylamide gel.

9. The method of claim 5 wherein the array, template, non-immobilized primer, and polymerase are cast in a polyacrylamide gel.

10. The method of claim 6 wherein the array, template, non-immobilized primer, and polymerase are cast in a polyacrylamide gel.

11. The method of either of claims 1 or 2 wherein said immobilized oligonucleotide primers of said array of step (a) are substantially pure in nucleic acid sequence.

12. The method of claim 2 wherein said immobilized oligonucleotide primers of the array of step (a) are heterogenous in nucleic acid sequence.

13. The method of claim 2 wherein said immobilized oligonucleotide primers are generated from genomic DNA.

14. The method of claim 3 wherein said immobilized oligonucleotide primers are generated from genomic DNA.

15. The method of claim 2 wherein the array, template, non-immobilized primer, and polymerase are cast in a polyacrylamide gel.

16. The method of claim 3 wherein the immobilized oligonucleotide primers are generated from genomic DNA.

17. The method of claim 1 wherein the non-immobilized oligonucleotide primer comprises a pool of oligonucleotide primers comprised of 5' and 3' sequence elements, said 5' sequence element identical in all members of said pool, and said 3' sequence element containing random sequences.

18. The method of claim 17 wherein the 5' sequence element comprises a restriction endonuclease recognition sequence.

19. The method of claims 17 wherein the 5' element comprises a transcriptional promoter sequence.

20. The method of claim 1 wherein the immobilized oligonucleotide primers of the array of step (a) are heterogenous in nucleic acid sequence.

21. The method of claim 1 wherein the immobilized oligonucleotide primers are generated from genomic DNA.

22. The method of claim 1 wherein the array, template, non-immobilized primer, and polymerase are cast in, a polyacrylamide gel.

23. The method claim 1 wherein the immobilized oligonucleotide primers of the array of step (a) are substantially pure in nucleic acid sequence.

24. The method of claim 1 wherein the non-immobilized oligonucleotide primers are heterogenous in nucleic acid sequence.

25. The method of claim 1 wherein the non-immobilized oligonucleotide primers are substantially pure in nucleic acid sequence.

26. The method of claim 1 wherein the immobilized oligonucleotide primers are heterogeneous with the non-immobilized oligonucleotide primers.

27. The method of claim 1 wherein the immobilized oligonucleotide primers are substantially pure in nucleic acid sequence with the non-immobilized oligonucleotide primers.

28. A method of amplifying a nucleic acid molecule, said method comprising the steps of:
   a) creating an array of immobilized oligonucleotide primers, wherein the primers are immobilized on a semi-solid support;
   b) hybridizing amplification template to an immobilized oligonucleotide primer,
   c) extending the immobilized oligonucleotide primer using a DNA polymerase activity, and deoxynucleotide triphosphates to form an immobilized nucleic acid strand and then denaturing the amplification template from the immobilized nucleic acid strand;
   d) hybridizing a non-immobilized oligonucleotide primer to the immobilized nucleic acid strand and extending the non-immobilized oligonucleotide primer and denaturing the extended nonimmobilized oligonucleotide primer from the immobilized nucleic acid strand, and
   e) repeating steps (b) and (c) and (d) for a defined number of cycles to yield a plurality of amplified nucleic acid molecules.

* * * * *

UNITED STATES PATENT AND TRADEMARK OFFICE
CERTIFICATE OF CORRECTION

PATENT NO. : 6,485,944 B1
DATED : November 26, 2002
INVENTOR(S) : George M. Church and Rob Mitra It is certified that error appears in the above-identified patent and that said Letters Patent is hereby corrected as shown below:

Column 1,
Line 3, after the title insert the following:

-- This invention was supported by DOE Grant No. DEFG02-87ER-60565 and the U.S. government has certain rights to the invention. --

Signed and Sealed this

Eleventh Day of March, 2003

JAMES E. ROGAN
*Director of the United States Patent and Trademark Office*

SEQUENCE LISTING

```
<160> NUMBER OF SEQ ID NOS:  9

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:T7 RNA
      polymerase binding sequence

<400> SEQUENCE: 1
taatacgact cactata                                                        17

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 2
tgcatgctat                                                                10

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 3
atagcatgca atgcatttac gtagc                                               25

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:hypothetical
      sequence
<221> NAME/KEY: unsure
<222> LOCATION: (27)..(32)
<223> OTHER INFORMATION: n equals a, t, c or g.

<400> SEQUENCE: 4
```

```
gcagcagtac gactagcata tccgacnnnn nn                                    32
```

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:hypothetical
      sequence
<221> NAME/KEY: unsure
<222> LOCATION: (27)..(32)
<223> OTHER INFORMATION: n equals a, t, c or g.

<400> SEQUENCE: 5

```
cgatagcagt agcatgcagg tccgacnnnn nn                                    32
```

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 6

```
tcggctcatc tgcatgctgc cagcagtcgg actacgtacc ccggtacgtg cgctacacgc      60
agcttt                                                                 66
```

<210> SEQ ID NO 7
<211> LENGTH: 88
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 7

```
gcagcagtac gactagcata tccgacctgc gtgtagcgca cgtaccgggg tacgtagtcc      60
gactgctggc agcatgcaga tgagccga                                         88
```

<210> SEQ ID NO 8
<211> LENGTH: 94
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 8

```
cgatagcagt agcatgcagg tccgaccagc agtcggacta cgtaccccgg tacgtgcgct      60
acacgcaggt cggatatgct agtcgtactg ctgc                                  94
```

<210> SEQ ID NO 9
<211> LENGTH: 94
<212> TYPE: DNA
<213> ORGANISM: Artificial Sequence
<220> FEATURE:
<223> OTHER INFORMATION: Description of Artificial Sequence:hypothetical
      sequence

<400> SEQUENCE: 9

```
gcagcagtac gactagcata tccgacctgc gtgtagcgca cgtaccgggg tacgtagtcc      60
gactgctggt cggacctgca tgctactgct atcg                                  94
```